United States Patent
Hurt, Jr. et al.

(10) Patent No.: US 9,145,553 B2
(45) Date of Patent: Sep. 29, 2015

(54) METHOD FOR ISOLATING NUCLEIC ACIDS

(71) Applicant: UT-Battelle, LLC, Oak Ridge, TN (US)

(72) Inventors: Richard Ashley Hurt, Jr., Knoxville, TN (US); Dwayne A. Elias, Knoxville, TN (US)

(73) Assignee: UT-BATTELLE, LLC, Oak Ridge, TN (US)

(*) Notice: Subject to any disclaimer, the term of this patent is extended or adjusted under 35 U.S.C. 154(b) by 40 days.

(21) Appl. No.: 13/918,201

(22) Filed: Jun. 14, 2013

(65) Prior Publication Data

US 2013/0338350 A1 Dec. 19, 2013

Related U.S. Application Data

(60) Provisional application No. 61/660,143, filed on Jun. 15, 2012.

(51) Int. Cl.
| | |
|---|---|
| *C07H 21/00* | (2006.01) |
| *B01L 3/00* | (2006.01) |
| *C12N 15/10* | (2006.01) |
| *C12Q 1/68* | (2006.01) |

(52) U.S. Cl.
CPC ............ *C12N 15/1003* (2013.01); *B01L 3/527* (2013.01)

(58) Field of Classification Search
CPC ............................. C12N 15/1003; B01L 3/527
USPC ................ 435/6.1; 422/430; 536/25.4, 25.41, 536/25.42
See application file for complete search history.

(56) References Cited

U.S. PATENT DOCUMENTS

2010/0105093 A1* 4/2010 Bugler et al. ................ 435/18

FOREIGN PATENT DOCUMENTS

CN 102409041 A * 4/2012

OTHER PUBLICATIONS

Nichols et al. (Journal of Food Protection, (Mar. 2004) vol. 67, No. 3, pp. 524-532). Abstract only.*
Andeer P. et al., "High-Sensitivity Stable-Isotope Probing by a Quantitative Terminal Restriction Fragment Length Polymorphism Protocol", Applied and Environmental Microbiology 78(1):163-169 (Jan. 2012).
Deangelis K.M. et al., "PCR Amplification-Independent Methods for Detection of Microbial Communities by the High-Density Microarray PhyloChip", Applied and Environmental Microbiology 77(18):6313-6322 (Sep. 2011).

(Continued)

*Primary Examiner* — Jezia Riley
(74) *Attorney, Agent, or Firm* — Scully, Scott, Murphy & Presser, P.C.

(57) ABSTRACT

The current disclosure provides methods and kits for isolating nucleic acid from an environmental sample. The current methods and compositions further provide methods for isolating nucleic acids by reducing adsorption of nucleic acids by charged ions and particles within an environmental sample. The methods of the current disclosure provide methods for isolating nucleic acids by releasing adsorbed nucleic acids from charged particles during the nucleic acid isolation process. The current disclosure facilitates the isolation of nucleic acids of sufficient quality and quantity to enable one of ordinary skill in the art to utilize or analyze the isolated nucleic acids for a wide variety of applications including, sequencing or species population analysis.

Figure 1:
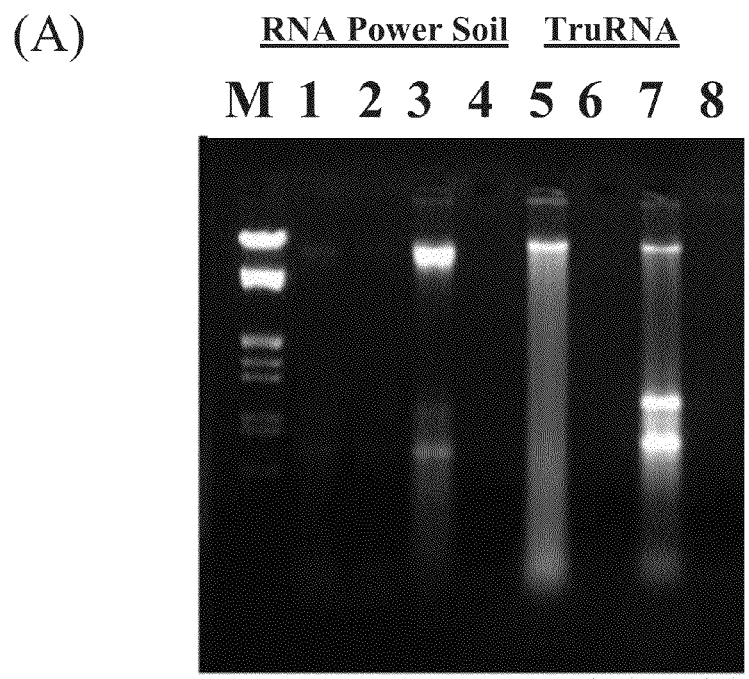
Figure 1:
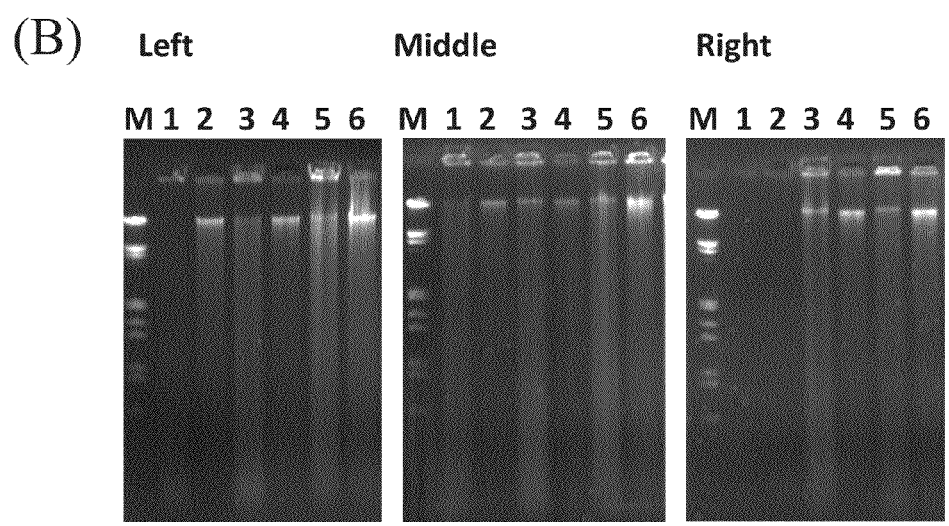

24 Claims, 8 Drawing Sheets
(4 of 8 Drawing Sheet(s) Filed in Color)

(56) References Cited

OTHER PUBLICATIONS

Direito S.O.L. et al., "Sensitive Life Detection Strategies for Low-Biomass Environments: Optimizing Extraction of Nucleic Acids Adsorbing to Terrestrial and Mars Analogue Minerals", FEMS Microbiol Ecol 81:111-123 (2012).

Gu B. et al., "Competitive Adsorption, Displacement, and Transport of Organic Matter on Iron Oxide: I. Competitive Adsorption", Geochmica et Cosmochimica Acta 60(11):1943-1950 (1996).

Gu B. et al., "Competitive Adsorption, Displacement, and Transport of Organic Matter on Iron Oxide: II. Displacement and Transport", Geochmica et Cosmochimica Acta 60(16):2977-2992 (1996).

Hurt R.A. et al., "Simultaneous Recovery of RNA and DNA from Soils and Sediments", Applied and Environmental Microbiology 67(10):4495-4503 (Oct. 2001).

Hwang C. et al., "Bacterial Community Succession During In Situ Uranium Bioremediation: Spatial Similarities Along Controlled Flow Paths", The ISME Journal 3:47-64 (2009).

Hwang C. et al., "Changes in Bacterial Community Structure Correlate with Initial Operating Conditions of a Field-Scale Denitrifying Fluidized Bed Reactor", Applied Microbiology Biotechnology 71:748-760 (2006).

Zhou J. et al., "DNA Recovery from Soils of Diverse Composition", Applied and Environmental Microbiology 62 (2):316-322 (Feb. 1996).

\* cited by examiner (A) 
(B)

SEQUENCE LISTING

```
<160> NUMBER OF SEQ ID NOS: 2

<210> SEQ ID NO 1
<211> LENGTH: 45
<212> TYPE: DNA
<213> ORGANISM: Artificial Sequence
<220> FEATURE:
<223> OTHER INFORMATION: Forward primer for the 16s rRNA gene region

<400> SEQUENCE: 1
cgtatcgcct ccctcgcgcc atcagagagt ttgatcctgg ctcag              45

<210> SEQ ID NO 2
<211> LENGTH: 47
<212> TYPE: DNA
<213> ORGANISM: Artificial Sequence
<220> FEATURE:
<223> OTHER INFORMATION: Reverse primer for the 16s rRNA gene region

<400> SEQUENCE: 2
ctatgcgcct tgccagcccg ctcagcgcaa ctyaccgcgg ctgctgg            47
```

METHOD FOR ISOLATING NUCLEIC ACIDS

CROSS REFERENCE TO RELATED APPLICATIONS

This application claims priority from U.S. Provisional Application No. 61/660,143, filed Jun. 15, 2012, the entire contents of which are incorporated herein by reference.

STATEMENT REGARDING FEDERALLY SPONSORED RESEARCH

The United States Government has rights in this invention pursuant to contract no. DE-AC05-00OR22725 between the United States Department of Energy and UT-Battelle, LLC.

FIELD OF THE DISCLOSURE

The present disclosure relates to methods for isolating nucleic acids from an environmental sample. The current disclosure also relates to detecting and characterizing organisms in an environmental sample based on the nucleic acids isolated therefrom. Nucleic acids isolated using the kits and methods of the present disclosure may be used in a wide variety of fields and applications, including but not limited to, detecting and characterizing organisms in an environmental sample.

BACKGROUND

High throughput sequencing technologies requiring higher quality and larger nucleic acid samples to analyze the existing microbial flora in an environmental sample are rapidly overtaking previously existing analytical methods in the field. The inability to recover nucleic acids of sufficient quantity and quality from iron oxide complexed clay limits nucleic acid based assessment of many environments. When comparing nucleic acid extraction procedures, a higher nucleic acid yield can indicate low sampling bias and thus a more complete assessment of the microbial community. See Cullen and Hirsch, *Soil Biology & Biochemistry*. (1998) 30: 983-993; Frostegard et al., *Appl. Environ. Microbiol.* (1999) 65: 5409-5420. However, nucleic acid isolation methods differ in their ability to recover nucleic acid from cells within a sample due to loss to adsorption of nucleic acids by cations present on the surface of clay particles in an environmental sample, making it difficult to judge microbial community coverage on the basis of nucleic acid yield.

For iron rich clays, DNA and RNA yields can be minimal or absent, primarily due to nucleic acid adsorption. The polyanionic property of nucleic acid is derived from the 5'-phosphate linkages and will support a large number of binding sites either directly with iron oxides or with multivalent cations bound to negatively charged clay particles. Therefore, it is reasonable to anticipate that longer nucleic acid polymers will have a larger number of ionic interactions with substrates carrying multiple positive charges, and thereby have increased binding strength with iron oxides. Other clay environments containing additional polyvalent cations associated with the negatively charged surface of clay particles can limit recovery as well.

The negative charge at the surface of clay particles can bind polyvalent cations and form an adsorptive bridge that binds nucleic acids. Carboxyl and hydroxyl groups of humic and fulvic acids form stable complexes with metal cations, with a binding strength order of $Fe^{3+}>Al^{3+}>Pb^{2+}>Ca^{2+}>Mn^{2+}>Mg^{2+}$. See Gu et al. *Environmental Science & Technology* (1994) 28: 38-46. A number of these metals, particularly $Al^{3+}$, are prevalent in clay materials and can reduce microbial activity. See Wong et al., *Microb. Ecol.* (2004) 47: 80-86.

A common method for extraction of DNA and RNA from clay as well as more typical soils would allow exploration of vast environments that are considered recalcitrant to molecular microbiological analysis. The current state of the art can be exemplified by extraction procedures using low concentrations (100 mM) of phosphate in the extraction buffer only hoping to promote desorption. See Zhao, J., et al., *Appl. Environ. Microbiol.* (1996) 62: 316-322); Hurt et al., *Appl. Environ. Microbiol.* (2001) 67: 4495-4503); Andeer et al., *Appl. Environ. Microbiol.* (2012). Moreover, Direito et al. used 1 M sodium phosphate and heat (≥55° C.) to recover DNA from Mars analogue substrates by lysis using a bead milling process. See Direito, S. O., et al., *FEMS Microbiol. Ecol.* (2012) 81: 111-123. Unfortunately, heating a solution containing nucleic acids leads to the denaturing and fragmentation of the nucleic acids resulting in smaller nucleic acids that are less useful in sequencing protocols. Moreover, sheering of DNA using bead milling lysis techniques results in smaller fragments of DNA that limit the ability to analyze the species diversity in a sample due to the difficulties inherent in sequencing of small DNA fragments (<15 kb).

Taken together, iron cemented clays and soils with a high humic acid content are notoriously difficult to isolate nucleic acids from in high molecular weights amenable to sequencing efforts. Thus, the current disclosure overcomes this issue by prohibiting adsorption and maximizing desorption of nucleic acids from the surface of charged clay particles.

SUMMARY OF THE DISCLOSURE

The present methods are premised on the discovery that the use of a concentrated sodium phosphate buffer in the isolation process can effectively counteract against the positive charges present in an environmental sample which are believed to prevent an effective recovery of nucleic acids (generally negatively charged) from the sample. The current disclosure provides methods for isolating nucleic acid from environmental samples that are otherwise recalcitrant to yielding nucleic acid residing within the sample. The data described herein demonstrate that after cell lysis, nucleic acid extraction and centrifugation, washing the sample pellet with a concentrated sodium phosphate buffer releases negatively charged nucleic acid previously adsorbed by the multivalent cations present on the surface of the environmental materials, thus maximizing desorption of the nucleic acid. The methods of the current disclosure further demonstrate that the addition of a sodium phosphate buffer during the cell lysis process inhibits adsorption of nucleic acid, resulting in a higher yield of nucleic acid from the sample. Taken together, the methods described herein show that treatment of a sample with concentrated sodium phosphate buffer facilitates both competitive desorption during post-lysis washing and inhibits nucleic acid adsorption during cell lysis resulting in the isolation of nucleic acids of sufficient quantity and quality that enable an in-depth analysis of the extant microbial community present in an environmental sample.

In some embodiments, a concentrated sodium phosphate buffer is used to wash lysed materials after the cell lysis and extraction steps to desorb any nucleic acid bound to positively charged particles during the lysis and extraction steps. In other embodiments, a sodium phosphate buffer is used in the lysis step to prevent adsorption of nucleic acids to positively charged particles in the sample. In additional embodiments, a sodium phosphate buffer is used in the lysis step and in a wash step. The present methods do not require heating during any step, are easy to implement, and have been demonstrated to efficiently isolate nucleic acid from environmental samples that are otherwise recalcitrant to yielding nucleic acid, at sufficient quantity and quality.

According to the present methods an environmental sample containing a biological entity or entities is obtained and the sample is subjected to a lysis process whereby the environmental sample is mixed with a lysis solution, optionally containing a sodium phosphate buffer, in the presence of liquid nitrogen. The resulting lysed material is then subjected to an extraction process whereby the lysed material is mixed with extraction solution and then separated into a sample pellet and a supernatant via centrifugation. The resulting supernatant containing extracted nucleic acids is collected and, optionally, the pellet is washed in a concentrated sodium phosphate buffer to desorb any nucleic acid bound to positively charged particles during the lysis and extraction processes. The supernatant from the wash is then collected and can be combined with the supernatant obtained from the extraction process, and the collected supernatant(s) can be treated with phenol/chloroform (or isoamyl alcohol) solution to further separate the nucleic acid from other cellular or environmental materials in the solution. Precipitation of the nucleic acid from solution via the addition of alcohol (e.g., isopropanol) and purification of the isolated nucleic acids by known methods or by washing with ethanol may then be carried out enabling the resulting nucleic acids to be utilized in many ways including, but not limited to, cloning and sequencing.

The current methods do not heat the sample at to a temperature that would denature the nucleic acid (i.e., above 35° C.) or employ lysis techniques that sheer nucleic acid (i.e., bead milling), and thus nucleic acid isolated by the current methods includes high molecular weight ($\geq$20 kb) nucleic acids. The isolated nucleic acid isolated via the current methods will be of sufficient quality and quantity enabling the nucleic acids to be analyzed as desired by the end user.

The methods and kits of the current disclosure are useful in a wide variety of fields and applications, including but not limited to, detecting and characterizing organisms in an environmental sample, and for systems biology studies including, but not limited to, microbial community genomic and transcriptomic studies.

BRIEF DESCRIPTION OF DRAWINGS AND TABLES

The file of this patent contains at least one drawing executed in color. Copies of this patent with color drawing(s) will be provided by the Patent and Trademark Office upon request and payment of the necessary fee.

FIG. 1. Reagent test and process development sample evaluation. (A) Ethidium bromide stained 1.2% agarose TAE electrophoresis image (3 V/cm×90 min) comparing reagent systems (Lanes 1-4: PowerSoil™ isolation kit (MoBio); Lanes 5-8: TruRNA™ Atom Sciences, Oak Ridge) used for stream sediment RNA or total nucleic acid (TNA) recovery. Lane M; Marker III™ (Roche®), lanes (1, 5) extraction product from NOAA sediment core, lanes (2, 6) extraction product from New Horizon sediment core, lanes (3, 7) extraction products from the A-horizon surface soil sample, lanes (4, 8) extraction products from the iron cemented clay sample. (B) Evaluation of lysis reagent additives. Electrophoretic images (Left, Middle, Right) taken from independent extraction experiments done in triplicate. Electrophoretic images are from a single 1.2% agarose gel using 0.1 µg/ml ethidium bromide in 1×TAE at 3 Vcm$^{-1}$ for 90 min. Lanes 1, 3, and 5 are 5% of the total direct extraction product DNA yield from 200 mg iron cemented clay (wet weight) performed using 0.33 volume of the modified lysis reagents containing sodium phosphate buffer. Lanes 2, 4, and 6 provide the results of washing the pellet obtained from the extracted clay samples shown in lanes 1, 3 and 5 with sodium phosphate buffer. Lanes 1 used lysis reagent containing 300 mM sodium phosphate buffer added to the standard lysis reagent with sarkosyl omitted. Lanes 3 show the result from standard lysis reagent supplemented with 300 mM sodium phosphate buffer and 1% sarkosyl. Lanes 5 show the result from standard lysis reagent supplemented with 300 mM sodium phosphate buffer, 1% sarkosyl, and 10% weight by volume (w/v) BSA.

Figure 2:
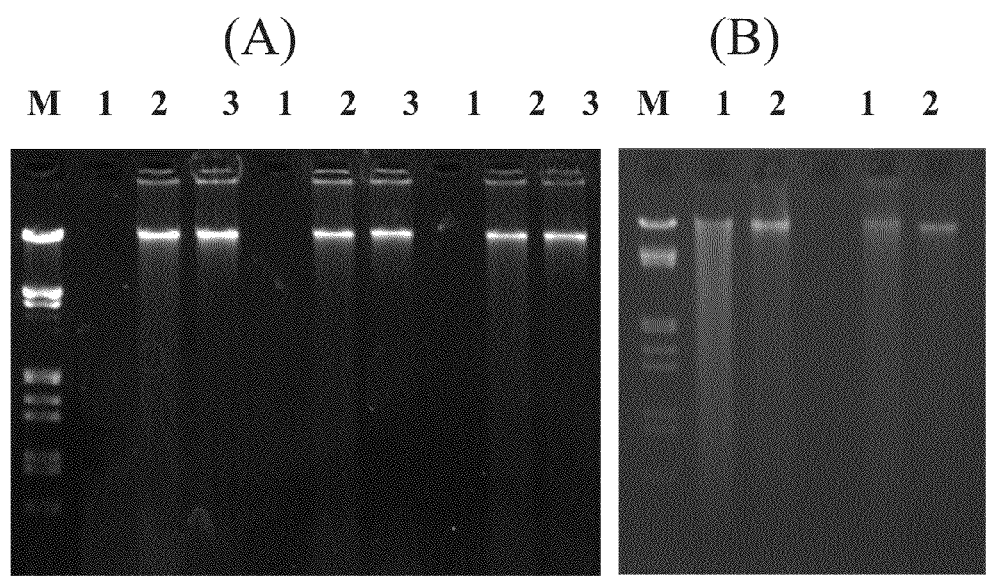

FIG. 2. Sodium phosphate buffer testing. (A) Sodium phosphate buffer pellet wash test. Lysis was done for 3 replicate extractions using lysis solution without sodium phosphate buffer (4 M guanidine thiocyanate; 100 mM MOPS (pH 7.0) 25 mM EDTA; 1% sarkosyl). Lanes 1, standard extraction process result from 200 mg iron cemented clay. Lanes 2, first of two clay pellet washes using 250 W sodium phosphate buffer (pH 7.0). Lanes 3, second clay pellet wash using 250 µl sodium phosphate buffer. Lane M; Marker III™ (Roche®). (B) Test with sodium phosphate buffer in the lysis reagent. Lanes 1; extraction result from lysis reagent containing 1 M sodium phosphate buffer and 6 M guanidine HCl followed by sample dilution in a concentrated salt based extraction buffer. Lanes 2; extraction result from lysis reagent containing 1 M sodium phosphate buffer and 6 M guanidine HCl followed by sample dilution in 1.4 ml urea based extraction buffer and subjecting the pellet to sodium phosphate buffer wash. Lanes M; Marker III™ (Roche®). Samples were electrophoresed for 90 min at 3 V/cm in 1×TAE buffer with 100 ng/ml ethidium bromide.

Figure 3:
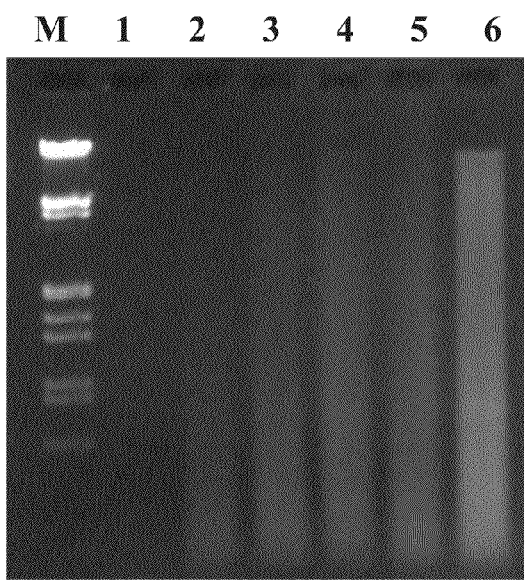
Figure 3:
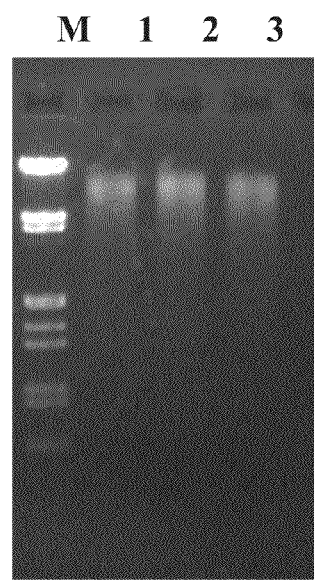

FIG. 3. Phosphate gradient test. (A) 1.2% agarose gel using 0.1 µg/ml ethidium bromide in 1×TAE at 3 V/cm for 90 min. Lanes 1-6 (1° extract); 0, 100 mM sodium phosphate buffer, 200 mM sodium phosphate buffer, 300 mM sodium phosphate buffer, 400 mM sodium phosphate buffer, and 500 mM sodium phosphate buffer in the lysis reagent, respectively. Ten percent of the total yield from the initial extraction process from 200 mg wet weight of the iron oxide cemented clay environment was examined in each lane. Lane M; Marker III™ (Roche®). (B) 1.2% agarose gel using 0.1 µg/ml ethidium bromide in 1×TAE at 4.7 V/cm for 90 min. Lanes 1-3; replicate extractions from 250 mg samples of the iron oxide cemented clay using the Powerlyzer™, PowerSoil™ DNA isolation kit (MoBio); 10% of the total yield was again examined. Lane M; Marker III™ (Roche®).

Figure 4:
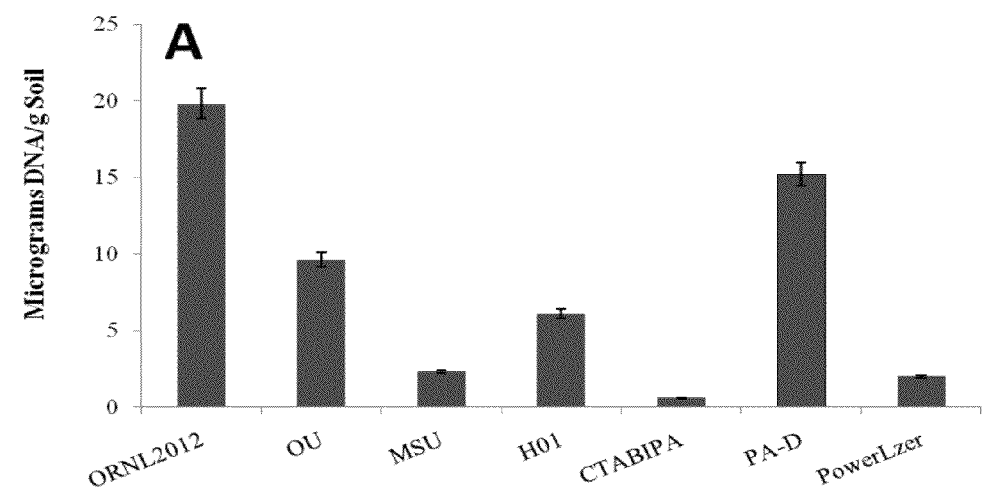
Figure 4:
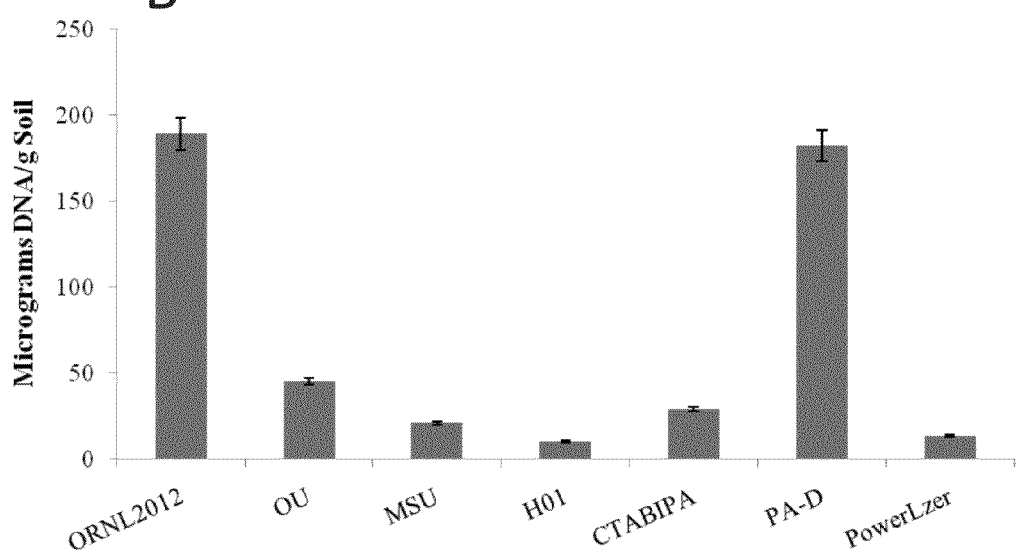
Figure 4:
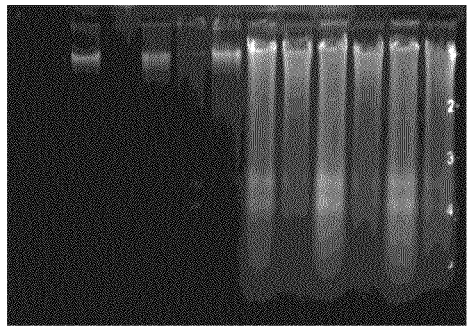
Figure 4:
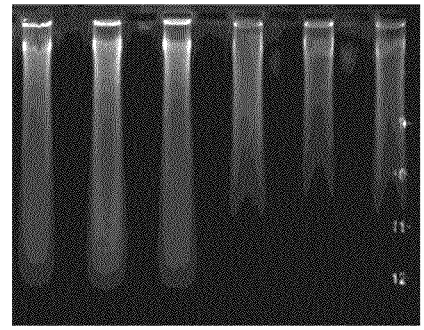

FIG. 4. Comparison of methods. (A), (B) Various published and commercial procedures were compared for total DNA recovery from clay (A) and A-horizon soils (B). Commercial kits included the Powerlyzer™ (PowerLzer), PowerSoil™ DNA isolation kit (MoBio) while the published methods included OU (See Zhao, J., et al., *Appl. Environ. Microbiol.* (1996) 62: 316-322), MSU (See Hwang, C. et al., *The ISME Journal* (2009) 3, 47-64), H01 (See Hurt et al., *Appl. Environ. Microbiol.* (2001) 67: 4495-4503), CTABIPA (See DeAngelis, K. M., et al., *Appl. Environ. Microbiol.* (2011) 77(18):6313.) and PA-D (See Andeer et al., *Appl. Environ. Microbiol.* (2012) 78: 163-169). (C) (D) Comparison of liquid nitrogen lysis grinding procedures. (C) Preparative electrophoresis gel containing triplicate extractions using the current methods from deciduous forest subsurface (Clay) and surface (A-horizon) environmental samples. Lanes marked 1 contain 50 µl of 200 µl primary extract from 250 mg sample. Lanes marked 2 contain 50 µl of 200 µl phosphate desorption product from 250 mg sample. (D) Preparative electrophoresis gel containing nucleic acids extracted using the OU procedure from deciduous forest subsurface (Clay) and surface (A-horizon) samples. Lanes marked 1, 2, and 3 contain 50 µl of 200 µl nucleic acid extract from triplicate 5 g soil samples.

Figure 5:
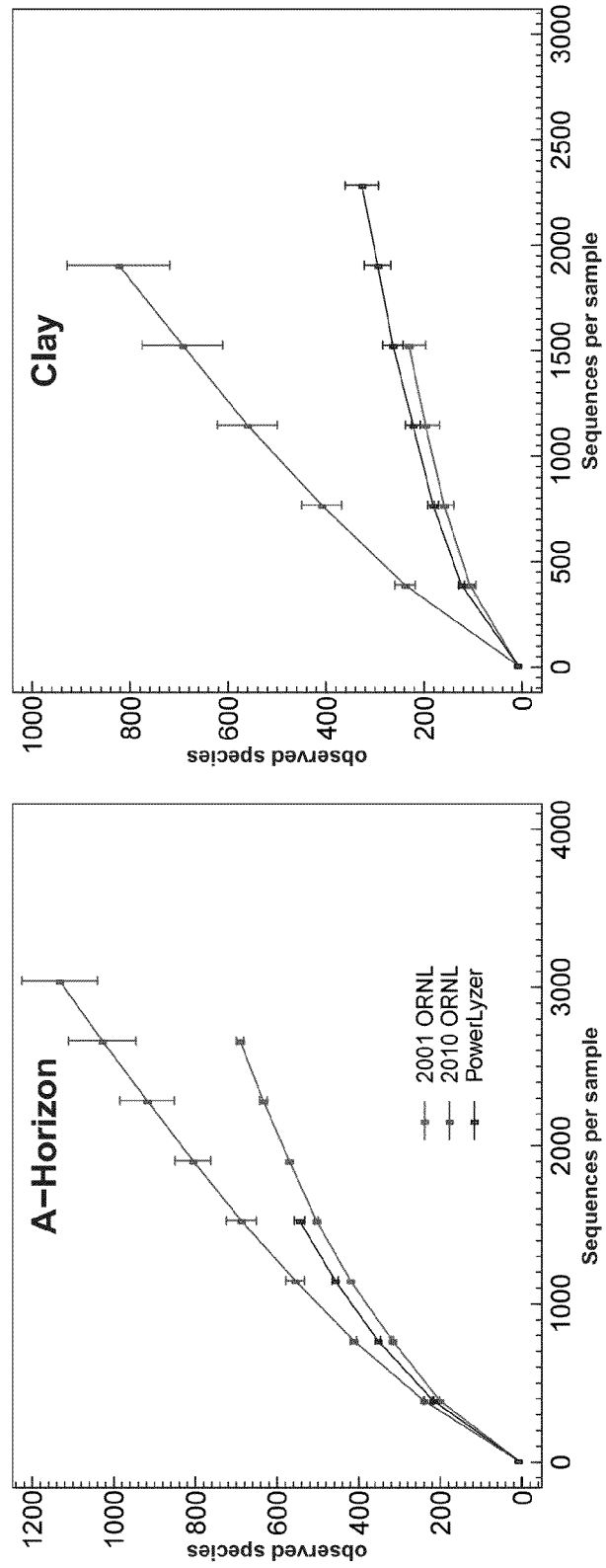

FIG. 5. Rarefaction based comparison of extraction procedures. Rarefaction analysis was done using the de-noised 454 pyrotag sequencing data. Each curve represents the average from experimental replicates conducted on A-horizon samples, N=2 libraries for 2001 ORNL and the method of the current disclosure (ORNL 2010); and N=3 libraries for the powerLyzer method. The legend for the clay sample representation is the same as the A-horizon comparison.

Figure 6:
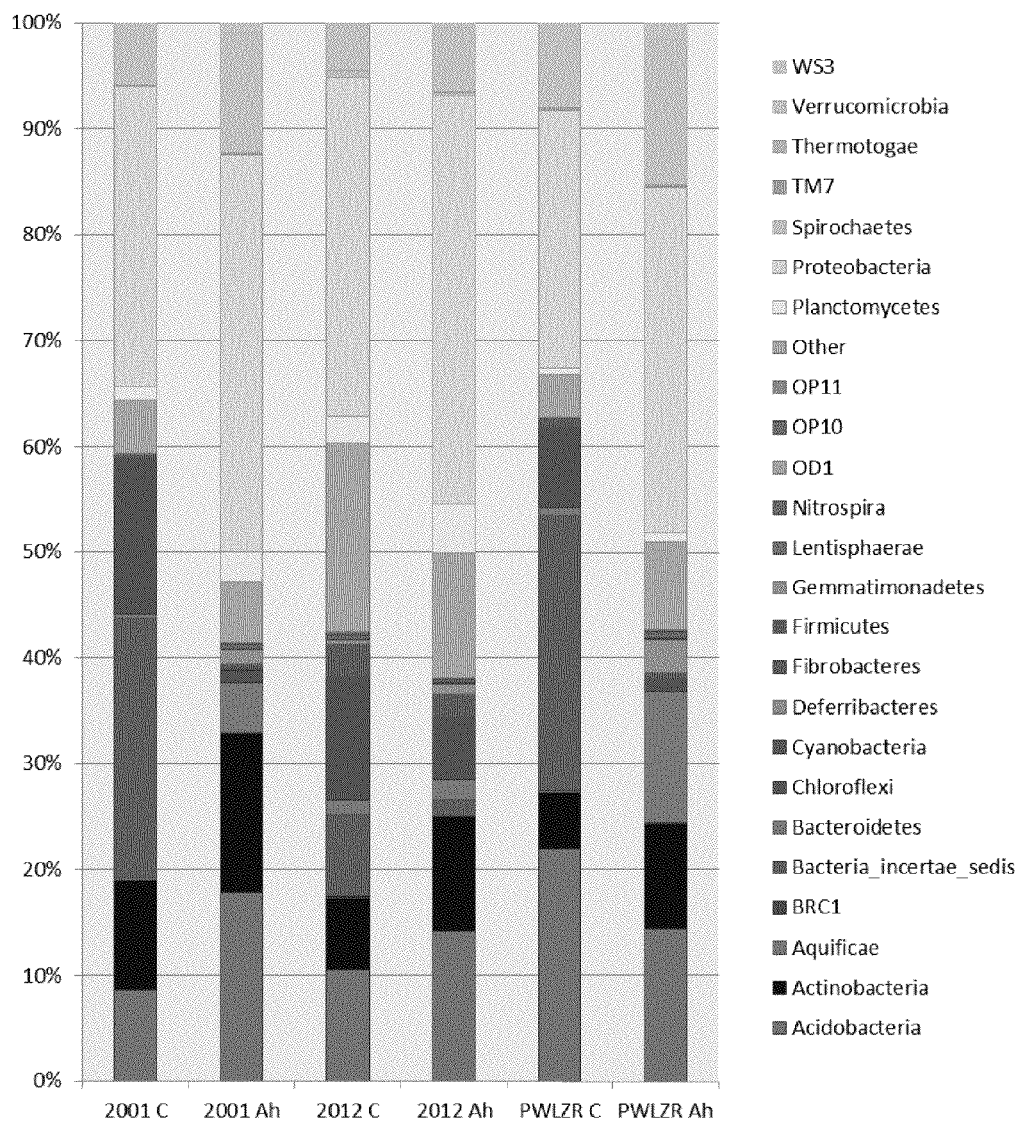

FIG. 6. 16S V1/V3 Phyletic dispersion. Phyletic dispersion of accessed microbial diversity derived from the RDP Classifier (See Cole, J. R., et al., *Nucleic Acids Research*. (2009) 37: D141-145) using a confidence threshold of 50% for OTU assignment of the de-noised 454 pyrotag sequencing data. Each lane is the average from experimental replicates (N=2 libraries for the 2001 method (See Hurt et al., 2001) and method of the current disclosure (2012) A-horizon samples; N=3 libraries for the remainder of the sample/method combinations. C=clay, Ah=A Horizon. PWLZR represents the samples extracted using the PowerLyzer™ System (MoBio). Phyla not represented by more than 1% of the total operational taxonomic units (OTU) for any of the methods analyzed were removed from the displayed comparison.

Figure 7:
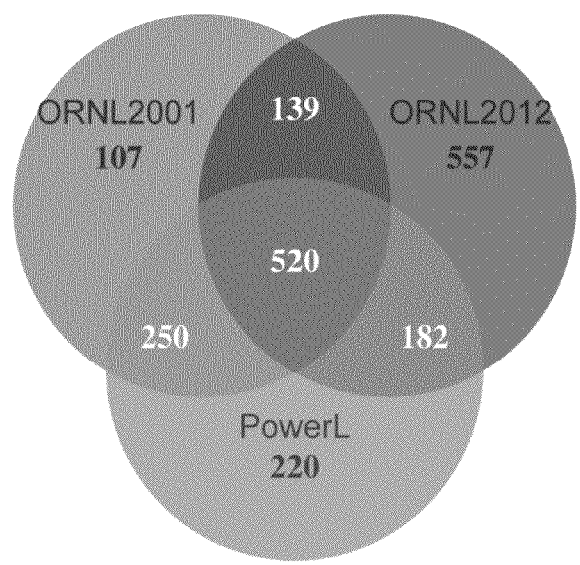
Figure 7:
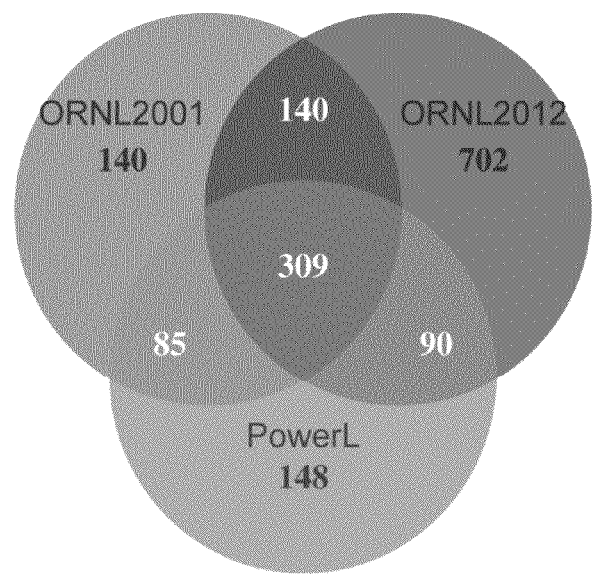

FIG. 7. OTU overlap among DNA extraction methods. Venn diagrams prepared using Mothur from the combined OTUs accessed using experimental replicate extractions from iron oxide cemented clay (left), and deciduous forest A-horizon soil (right). OTUs were from de-noised 454 pyrotag sequencing data with singletons identified as occurring only once across all methods for a given environment removed.

Table 1. Comparison of Methods by Rarefaction Results at 2500 and 5000 Sequences.

$^A$ Data is the average (OTU's/read) among replicate extractions. $^B$ Data from 4900 sequences because of read number termination. $^C$ Two PowerLyzer™ extraction product libraries terminated prior to 5000 reads.

Table 2. Basic Sample Chemistry.

$^A$ Acid extractable Fe. $^B$ Extractable Fe or Al following digestion of 0.5 g soil with concentrated $HNO_3$ (1 mL) and HCl (0.5 mL).

Table 3. Extraction Method Comparison.

Nucleic acid extraction methods were conducted and compared to the method of the current disclosure for quality and quantity of nucleic acid isolates.

DETAILED DESCRIPTION OF THE DISCLOSURE

The current disclosure provides methods for isolating nucleic acid from environmental samples that are otherwise recalcitrant to yielding nucleic acid residing within the sample. The present methods are premised on the discovery that the use of a concentrated sodium phosphate buffer in the isolation process can effectively counteract against the positive charges present in an environmental sample which are believed to prevent an effective recovery of nucleic acid (generally negatively charged) from the sample. The data described herein demonstrate that after cell lysis, nucleic acid extraction and centrifugation, washing the resulting sample pellet with a concentrated sodium phosphate buffer releases negatively charged nucleic acid previously adsorbed by the multivalent cations present on the surface of the environmental materials, thus maximizing desorption of the nucleic acid. The methods of the current disclosure further demonstrate that the addition of sodium phosphate buffer during the cell lysis process inhibits adsorption of nucleic acid, resulting in a higher yield of nucleic acid from the sample. Taken together, the methods described herein show that treatment of a sample with concentrated sodium phosphate buffer facilitates both competitive desorption during post-lysis washing and inhibits nucleic acid adsorption during cell lysis resulting in the isolation of nucleic acids of sufficient quantity and quality that enable an in-depth analysis of the extant microbial community present in an environmental sample.

TERMINOLOGY

As used herein the term "environmental sample" or "sample", refers to a sample containing material from the natural environment. The natural environment is meant to encompass the biosphere, or any environment containing positively charged particles or materials wherein genetic material may be found. Specifically, the environmental sample contains positively charged particles and genetic material including, nucleic acids. Environmental samples include, but are not limited to, samples taken from any soil (encompassing all of the soil types and depths), water or liquid (encompassing all freshwater aquatic, or marine habitats), sediment (encompassing marine sediment, lake or river sediment, or mud sediment) or atmospheric dust or particulate. In an aspect of the current disclosure an environmental sample contains a multitude of species or a single species. As used herein, species refers to any taxonomic grouping of genetically distinct organisms. Species and organisms need not be living organisms, but merely possess genetic material in the form of nucleic acid.

The term "soil" as used herein refers to environmental samples of soil, manure, compost, and the like, e.g., commercial potting mixtures, commercial soil amendments. The term also includes a broad range of organic carbon and nitrogen content and varying sand, silt and/or clay compositions. Soil as used herein includes any composition containing components commonly associated with habitable and uninhabitable areas of the earth, including for example varying descriptions, e.g., dust, dirt, mud, muck, silt, ground, compost, composting landfills at various depths. Non-limiting examples of soil include landfill (e.g., 0-3 inches deep or 3-6 inches deep); A-horizon soil; animal manure (e.g., horse manure); mulch, e.g., mulch top soil; the ocean floor, hillsides, mountaintops and may extend from the surface to any depth.

"A-horizon" or "topsoil" as used in the current disclosure shall mean a soil layer having formed at the surface (e.g., 0-12 inches deep) exhibiting obliteration of all or much of the original rock structure and show one or both of the following; an accumulation of humified organic matter intimately mixed with the mineral fraction, or properties resulting from cultivation, pasturing, or similar kinds of disturbance.

The term "sediment" as used herein means particles, fragments or portions of inorganic or organic material that are transported and deposited by natural means (e.g., water, wind, glacial action, or gravity) that settle within a body of water (e.g., a lake, marine environment, river, or marsh). Non-limiting examples of sediment as used in the methods of the current disclosure include, marine sediment; river sediment, lake sediment and mud sediment deposited within slow moving bodies of water or standing water. Specific examples of sediment deposits for use in the current methods include, but are not limited to, sand, river runoff, silt, mud or clay deposits at the bed or shelf of a body of water.

The term "clay sample" as used in the current disclosure means an earthy environmental sample containing a combination of aluminum ($Al^{3+}$), iron ($Fe^{3+}$ and/or $Fe^{2+}$) and humic acids. Humic acids as used herein refer to any dibasic or tribasic acid containing carboxyl and phenol functional groups. Humic acids result from the degradation of organic material, such as plants, animals or detritus. Humic acid or humic acids as used in the current disclosure include fulvic acids and other low molecular weight acids capable of forming ionic complexes with positively charged ions present in soil or sediments including, but not limited to, magnesium ($Mg^{2+}$), manganese ($Mn^{2+}$), calcium ($Ca^{2+}$), lead ($Pb^{2+}$) and Fe. Humic acids are naturally occurring, polyelectrolytic, heterogeneous, organic substances that are generally dark brown in color, of relatively high molecular weight and, typically, resistant to degradation. Humic acids are found in water, air-borne organic materials, soils and sediments, and inhibit enzymatic (polymerase) activities characteristic of nucleic acid amplification techniques such as the polymerase chain reaction (PCR). Soils and sediments containing high organic carbon content also contain high levels of humic and fulvic acids. A clay sample may contain crystalline iron oxide. "Crystalline iron oxide" as referred to herein shall mean the naturally occurring mineral, specular hematite having the chemical formula, $Fe_2O_3$. Crystalline iron oxide is also commonly referred to as Specularite, iron oxide, ferric oxide, iron(III) oxide dehydrate or diiron trioxide.

The term "nucleic acid" as used herein refers to one or more nucleic acids of any kind, including single- or double-stranded forms. In one aspect of the current disclosure a nucleic acid is DNA and in another aspect the nucleic acid is RNA. In practicing the methods of the current disclosure, nucleic acid isolated by the present method is originated from one or more biological entities (e.g., viruses, cells, organisms) in a sample (i.e., an environmental sample). Wherein a biological entity as used herein means any independent organism or thing, alive or dead, containing genetic material (e.g., nucleic acid) that is capable of replicating either alone or with the assistance of another organism or cell. Non-limiting examples of sources for nucleic acid containing biological entities of the current disclosure include an organism or organisms including, a cell or cells, bacteria (e.g., Gram positive or Gram negative), yeast, fungi, algae, viruses, and Firmicutes. Nucleic acid isolated using a kit or method of the current disclosure can be from any cell containing organism or portion thereof, including, but not limited to bacteriophages, plasmids, spores, algae, nematodes, protozoa, prokaryotic cells, eukaryotic cells (such as fungal, insect or mammalian cells). DNA or RNA detected or isolated using a kit or method of the current disclosure is not necessarily located within a specific organelle but may be found in the cytoplasm, chloroplasts, mitochondria and nuclei of eukaryotic and multicellular organisms including mammals. Specifically, an organism of the current disclosure includes bacteria, algae, viruses, fungi, and mammals (e.g., humans).

As used herein the term "Gram negative bacteria" means any bacteria having a cell envelope with an additional outer membrane facing the external environment composed of phospholipids and lipopolysaccharides. Gram-negative bacteria are identified by their inability to retain the crystal violet dye in the Gram stain protocol. Thus, Gram negative bacteria appear red or pink following a Gram stain procedure. Non-limiting examples of Gram negative bacteria that can be detected and/or whose nucleic acid can be isolated using the kits and methods of the invention include but are not limited to Gram negative rods (e.g., anaerobes such as bacteroidaceae (e.g., *Bacteroides fragilis*), facultative anaerobes, enterobacteriaceae (e.g., *Escherichia coli*), vibrionaceae (e.g., *Vibrio cholerae*), pasteurellae (e.g., *Haemophilus influenzae*), and aerobes such as pseudomonadaceae (e.g., *Pseudomonas aeruginosa*); Gram negative cocci (e.g., aerobes such as Neisseriaceae (e.g., *Neisseria meningitidis*) and Gram negative obligate intracellular parasites (e.g., Rickettsiae (e.g., *Rickettsia* spp.). Examples of Gram negative bacteria families that can be detected and/or whose nucleic acid can be isolated include, but are not limited to, Acetobacteriaceae, Alcaligenaceae, Bacteroidaceae, Chromatiaceae, Enterobacteriaceae, Legionellaceae, Neisseriaceae, Nitrobacteriaceae, Pseudomonadaceae, Rhizobiaceae, Rickettsiaceae and Spirochaetaceae.

As used herein the term "Gram positive bacteria" means any bacteria that retains crystal violet dye and thus appears dark blue of violet following the Gram stain procedure. Examples of Gram positive bacteria that can be detected and/or whose nucleic acid can be isolated using the kits and methods of the current disclosure include, but are not limited to, *Firmicutes, A. globiformis, B. subtilis, C. renale, M. luteus, R. erythropolis*, Ea39, Ben-28 and *S. lividans*. Gram positive bacteria that can be detected and/or whose nucleic acid can be isolated also are in groups that include, for example, *Corynebacterium, Mycobacterium, Nocardia; Peptococcus* (e.g., *P. niger*); *Peptostreptococcus* (e.g., *Ps. Anaerobius*); and some species in the group are capable of fermentation, reduction of nitrate, production of indole, urease, coagulase or catalase); *Ruminococcus; Sarcina; Coprococcus; Arthrobacter* (e.g., *A. globiformis, A. citreus* or *A. nicotianae*); *Micrococcus* (e.g., *M. luteus, M. lylae, M. roseus, M. agilis, M. kristinae* and *M. halobius*); *Bacillus* (e.g., *B. anthracis, B. azotoformans, B. cereus, B. coagulans, B. israelensis, B. larvae, B. mycoides, B. polymyxa, B. pumilis, B. stearothormophillus, B. subtilis, B. thuringiensis, B. validus, B. weihenstephanensis* and *B. pseudomycoides*); *Sporolactobacillus; Sporocarcina*; Filibacter; Caryophanum and *Desulfotomaculum*. Other Gram positive bacteria that can be detected and/or whose nucleic acid can be isolated fall into the group *Clostridium*, which often include peritrichous flagellation, often degrade organic materials to acids, alcohols, $CO_2$, $H_2$ and minerals (acids, particularly butyric acid, are frequent products of clostridial fermentation), and in one aspect form ellipsoidal or spherical endospores, which may or may not swell the sporangium. Species of *Clostridium* that can be detected and/or whose nucleic acid can be isolated include psychrophilic, mesophilic or thermophilic species, saccharolytic species, proteolytic species and/or specialist species, and those that are both saccharolytic and proteolytic species. Saccharolytic species of *Clostridium* that can be detected and/or whose nucleic acid can be isolated include but are not limited to *Cl. aerotolerans, Cl. aurantibutyricum, Cl. beijerinckii, Cl. botulinum, Cl. butyricum, Cl. chauvoei, Cl. difficile, Cl. intestinale, Cl. novyi A, Cl. pateurianum, Cl. saccharolyticum, Cl. septicum, Cl. thermoaceticum*, and *Cl. thermosaccharolyticum*.

A "nucleic acid library" or "library", as used herein, refers to a compilation of genetic constructs, each comprising a DNA or RNA fragment stably inserted into a genetic vector whereby, the nucleic acid containing construct is capable of replication within a host organism. In one aspect the nucleic acid library or library is a DNA expression library, wherein the DNA fragment of interest is operably inserted into an expression vector (e.g., cloning), such that the DNA fragment is capable of being transcribed and translated into a polypeptide.

The term "amplicon" as used herein shall mean nucleic acid sequences that are formed as a result of natural or artificial nucleic acid amplification or replication. For example, a nucleic acid sequence may be amplified as a result of polymerase chain reaction (PCR) or gene duplication events.

The term "high molecular weight" as used in the current disclosure means nucleotides greater than or equal to 20,000 base pairs (bp) in length. High molecular weight nucleic acids range between 20 kilobase pairs (kb) and 500 kb, inclusive. In one example high molecular weight nucleic acid length is between 20 kb and 100 kb, inclusive. In yet another embodiment high molecular weight nucleic acid is between 20 kb and 50 kb, inclusive.

The term "sodium phosphate buffer" or "phosphate buffer" as used herein shall mean a solution containing any of the following alone or in combination: $NaH_2PO_4$, $Na_2HPO_4$, $Na_3PO_4$, at a pH between 7 and 9, inclusive. Non-limiting examples include 0.5 M $NaH_2PO_4$ with 0.5 M $Na_2HPO_4$ at pH 7.2 (wash buffer). In certain embodiments the sodium phosphate buffer exists at a pH between 7.0 and 9.0, inclusive. In yet another aspect of the current disclosure sodium phosphate buffer is between 0.3 M and 1.2 M, or between 0.5M to 1.1M, of $NaH_2PO_4$ with $Na_2HPO_4$ at pH of about 7.0. In one aspect of the current disclosure sodium phosphate buffer is 1M $NaH_2PO_4$ with $Na_2HPO_4$ at a pH between 7.0 and 8.0, inclusive. In certain aspects of the current methods sodium phosphate buffer is 1M $NaH_2PO_4$ with $Na_2HPO_4$ at pH 8.0 and 1M $NaH_2PO_4$ with $Na_2HPO_4$ at pH 7.2.

"Adsorption" or "adsorb" as used herein shall mean generally, the binding or adhesion of molecules, ions or particles to a solid surface. The binding of a molecule to the surface of a solid is reversible when the bonds formed between the solid surface and the adsorbent are broken. A non-limiting example of adsorption as used in the current disclosure is the adhesion of a negatively charged nucleic acid to the positively charged surface of a clay particle or soil sample.

The term "desorption" or "desorb" as used in the current disclosure means the release of a bound ion, molecule or particle adhered to the surface of a solid. Desorption can occurs as a result of competitive entities (ions, molecules or particles) replacing previously bound entities or the dissociation of adsorbed materials from the surface to which they are bound. Non-limiting examples of desorption as referenced in the current methods includes, the release of adsorbed nucleic acids from the charged surface of clay particles.

The term "agent" is employed herein to refer to any kind of compound, molecule or ion and any combination thereof. In one embodiment of the disclosure the agent is a small molecule. In another embodiment of the disclosure, the agent is a biological molecule, including, but not limited to, a protein or a peptide or a nucleic acid, or an ion. In another embodiment, the agent is a capable of binding charged ions in solution (e.g., chelation). In yet another embodiment, the agent changes the pH of a solution or mixture (e.g., buffering).

The term "peptide" or "protein" refers to a linear series of amino acid residues linked to one another by peptide bonds between the alpha-amino and carboxy groups of adjacent amino acid residues.

The term "binding", "to bind", "binds", "bound" or any derivation thereof refers to any stable, rather than transient, chemical bond between two or more molecules, including, but not limited to, covalent bonding, ionic bonding, and hydrogen bonding. Thus, this term also encompasses interaction between a nucleic acid molecule and a positively charged particle such as a cation or other positively charged agents.

Isolation Method

Conventional nucleic acid isolation procedures generally involve cell lysis and extraction with a combination of denaturing agents, chelating agents, proteolytic enzymes and non-ionic or anionic detergents and buffers. Following lysis and extraction and a subsequent centrifugation, the nucleic acids are separated from the supernatant via treatment with phenol/chloroform (or isoamyl alcohol) solution, to remove most of the undesirable cell lysis byproducts. The nucleic acid is then precipitated out of solution by the addition of alcohol (e.g., isopropanol), and optionally further purified by a variety of known methods including, but not limited to, treatment with ethanol. Unfortunately, nucleic acid isolation from environmental samples containing positively charged particles, such as, $Al^{3+}$, $Fe^{2+}$ or $Fe^{3+}$, and $Mg^{2+}$ results in nucleic acid yields that are severely reduced or absent all together due to adsorption of the nucleic acids to the positively charged particles.

The current methods provide a nucleic acid isolation process by which nucleic acid is efficiently isolated from an environmental sample. The present methods are premised on the discovery that the use of a concentrated sodium phosphate buffer in the isolation process can effectively counteract against the positive charges present in an environmental sample. In some embodiments, a concentrated sodium phosphate buffer is used to wash lysed materials after the cell lysis and extraction steps to desorb any nucleic acid bound to positively charged particles during the lysis and extraction steps. In other embodiments, a sodium phosphate buffer is used in the lysis step to prevent adsorption of nucleic acids to positively charged particles in the sample. In additional embodiments, a sodium phosphate buffer is used in both the lysis step and a wash step. The present methods do not require heating during any step, are easy to implement, and have been demonstrated to efficiently isolate nucleic acid from environmental samples that are otherwise recalcitrant to yielding nucleic acid, at sufficient quantity and quality.

According to the present methods, an environmental sample is obtained and the sample is subjected to a lysis process whereby the environmental sample is mixed with a lysis solution, optionally containing a sodium phosphate buffer, in the presence of liquid nitrogen. The resulting lysed material is then subjected to an extraction process whereby the lysed material is mixed with extraction solution and separated into a sample pellet and a supernatant via centrifugation. The resulting supernatant containing extracted nucleic acid is collected and the remaining pellet is washed in a concentrated sodium phosphate buffer, at least once to desorb any nucleic acid bound to positively charged particles during the lysis process. The supernatant from the wash is then collected and can be combined with the supernatant obtained from the extraction process, and the collected supernatant(s) can be treated with phenol/chloroform (or isoamyl alcohol) solution to further separate the nucleic acids from other cellular or environmental materials (e.g., denatured proteins, organelle membranes and/or environmental material). The extracted nucleic acids present in an aqueous (top) layer, are precipitated out of solution via the addition of alcohol (e.g., isopropanol) and purified by known methods or by washing with ethanol.

Sample Collection

An environmental sample may be collected by any means known to one of ordinary skill in the art or by using any commercially available or improvised method, and tested directly or stored prior to use. Non-limiting examples of sample collection techniques for use in the current methods are exemplified in Colwell, *Human pathogens in the aquatic environment*, pp. 337-344 In Colwell and Foster (eds.). Aquatic Microbial Ecology (1979); Fenical and Jenson, Marine Microorganisms: A New Biomedical Resource. (1992) Advances in Marine Biotechnology, vol. I: Pharmaceutical and Bioactive Natural Products, pp. 419-457, D.

Attaway, O. Zaborsky eds., Plenum Press, New York; Giovannoni et al., Nature (1990) 345:60-63; Griffiths et al. Microbial Ecol. (1996) 31:269-280; Suzuki et al., Appl. Environ. Microbiol. (1997) 63:983-989; Torsvik et al., *In Ritz and Giller* (eds.) *Beyond the Biomass: Compositional and Functional Analysis of Soil Microbial Communities*. (1994) John Wiley and Sons, Chichester; Ward et al., Nature (1990) 345: 63-65. In one aspect, nucleic acid is extracted using a kit or method of the invention at the site of collection, or the sample may be stored before a nucleic acid is isolated therefrom. Specifically, the environmental sample may be frozen and stored at a temperature between −60° C. to −80° C., inclusive. Alternatively, the sample may be stored at a temperature below or equal to 35° C. until use.

In one aspect of the current methods, stream sediment core samples consisting of a mixture of gravel and iron cemented clay were obtained from a stream or creek bed at a depth of 45 cm below the surface. The cores were frozen in the field in liquid nitrogen and stored at −80° C. until subjected to nucleic acid isolation processes. In yet another aspect of the current disclosure, the environmental sample was obtained from deciduous forest A-horizon soil. In certain aspects A-horizon environmental samples were placed in a plastic bag and root and other large material (e.g., rocks, gravel, leaves) were removed. The residual soil was then manually mixed to prepare a uniform soil sample. In one embodiment, the environmental sample obtained was iron cemented clay of uniform texture and a consistent moisture content of 24%, which was extracted from greater than 15 cm below the surface of A-horizon soil and maintained at a temperature below 35° C. until subjected to a nucleic acid isolation processes.

In certain aspects, clay samples for use in the current methods were obtained from larger environmental samples by cutting away exterior portions of the environmental sample using a sterile spatula and extracting a smaller portion of clay. In specific embodiments, the clay sample used in the current methods is between 0.1 g-0.5 g, 0.2 g to 2 g, 0.1 g and 5 g, inclusive, or greater than 5 g.

Lysis Process

In one embodiment of the current disclosure, the sample is subjected to a lysis process. The sample is mixed with a lysis solution in the presence of liquid nitrogen thereby obtaining lysed material. In certain aspects of the current disclosure the lysis solution contains a denaturing agent, an ionic buffer, and a chelating agent. A denaturing agent can be any agent known to one of ordinary skill in the art that disrupts or destroys the secondary and tertiary structure of a protein or proteins or other cellular material, excluding nucleic acids. Non-limiting examples of denaturing agents for use in the current methods include those used in conventional cell lysis solutions, such as, strong acids or bases, concentrated salts (e.g., NaCl), or organic solvents that when applied to cells disrupts the interactions (e.g., covalent or non-covalent bonds, Van der Waals interactions, hydrogen bonding) between the amino-acid side chains of proteins and/or the alpha-helical and beta-sheet patterns of cellular proteins. Specifically, denaturing agents of the current methods include, but are not limited to, urea, guanidine chloride, guanidine HCL, guanidine isothiocynanate, phenol, 2-mercaptoethanol, ethanol, methanol, acetic acid, trichloroacetic acid, sulfosalicylic acid, or dithothreitol. Denaturing agents can be applied to in any concentration appropriate to denature proteins or cellular materials, such as membranes. The concentration of denaturing agents to be used will vary depending on the amount and volume of sample being processed. Non-limiting examples of functional concentrations of denaturing agents for use in the current methods include, 4 to 6 M guanidine isothiocyanate, 4 to 6 M guanidine HCl, 5 to 20 ul/ml of 2-mercaptoethanol, and 1 to 4 M NaCl, inclusive.

Nucleic acids are sensitive to pH. At a high pH (pH>9) DNA is known to denature and the form single stranded DNA (ssDNA), meanwhile, at low pH DNA will depurinate, which dissociates the double helix structure by hydrolyzing the phosphodiester backbone. Thus, it is important to maintain a neutral pH (pH between 6.0 and 9.0) in solutions when working with nucleic acids. In certain aspects of the current methods ionic buffers are used to maintain a neutral pH that will not denature the nucleic acid being isolated. Ionic buffers are any solution or agent that when present in a mixture maintains a stable, neutral pH between 6.0 and 9.0, inclusive. Ionic buffers can be applied in any concentration necessary to maintain a neutral pH in solution. The concentration of ionic buffer to be used will vary depending on the amount and volume of sample being processed, as well as the composition of a solution. Non-limiting examples of functional concentrations of ionic buffer for use in the current methods include, 50 to 500 mM Tris(hydroxymethyl)aminomethane (Tris), 50-500 mM 3-(N-morpholino)propanesulfonic acid (MOPS), 50-500 mM 2-[4-(2-hydroxyethyl)piperazine-1-yl] ethanesulfonic acid (HEPES), inclusive. Non-limiting examples of ionic buffers for use in the current methods include, but are not limited to, Tris(hydroxymethyl)aminomethane (Tris), 3-(N-morpholino)propanesulfonic acid (MOPS), 2-[4-(2-hydroxyethyl)piperazine-1-yl]ethanesulfonic acid (HEPES).

During cell lysis, metal dependent enzymes are released that when active may interact with, damage, and denature nucleic acids or proteins. Thus, in certain embodiments of the current disclosure, a chelating agent is added to the lysis solution to bind metal ions thereby inhibiting the activity of cation dependent enzymes and maintaining the integrity of nucleic acid. Specific examples of chelating agents for use in the current methods include, but are not limited to, ethylenediaminetetraacetic acid (EDTA), ethylene glycol tetraacetic acid (EGTA) and ethylenediamine. Chelating agents can be applied in any concentration necessary to competitively bind ionic material in a solution of the current disclosure. The concentration of chelating agents to be used will vary depending on the amount and volume of sample being processed. Non-limiting examples of functional concentrations of chelating agents for use in the current methods include, 5 to 500 mM EDTA, inclusive.

In one aspect of the current methods the lysis solution contains a detergent. Detergent when added to the lysis solution causes the cell membrane to break down by dissolving the lipids and proteins of the cell and disrupting the bonds that maintain the integrity of the membrane. Detergent then interacts with the denatured lipids and proteins, causing them to precipitate out of solution. Non-limited examples of detergents for use in the current methods include, sodium dodecyl sulfate (SDS), sarkosyl, sodium lauryl sarcosinate, cetyltrimethyl ammonium bromide (CTAB), cholic acid, deoxycholic acid, benzamidotaurocholate (BATC), octyl phenol polyethoxylate, polyoxyethylene sorbitan monolaurate, tert-octylphenoxy poly(oxyethylene)ethanol, 1,4-piperazinebis-(ethanesulfonic acid), N-(2-acetamido)-2-aminoethanesulfonic acid, polyethylene glycol tert-octylphenyl ether (Triton® X-100), (1,1,3,3-tetramethylbutyl)phenyl-polyethylene glycol (Triton® X-114) and any combination thereof. Detergents can be applied to in any concentration necessary to break down the membrane of cells within an environmental sample. The concentration of detergent to be used will vary depending on the amount and volume of sample being processed. Non-limiting examples of functional concentrations of detergents for use in the current methods include, 0.1% to 10% weight by volume sarkosyl (including 0.1%, 0.5%, 1%, 5%, and 10% w/v, for example), and 0.1% to 10% weight by volume CTAB (including 0.1%, 0.5%, 1%, 5%, and 10% w/v, for example).

In another embodiment serum albumin protein is added to the lysis solution. Serum albumin is commonly used to stabilize enzymes and prevent adhesion of molecules to reaction tubes, thus in certain instances it is beneficial to add serum albumin protein to the lysis solution. Specific examples of serum albumin for use in the current methods include, but are not limited to, human albumin serum and bovine albumin serum (BSA). Serum albumin can be added to solution at any concentration necessary to stabilize enzymes or prevent the adhesion of molecules to reaction materials (e.g., centrifuge tubes or collection devices). Non-limiting examples of functional concentrations of serum albumin for use in the current methods includes, 1% to 25% weight by volume BSA (including 1%, 5%, 10%, 15%, 20% and 25%, for example).

During cell lysis negatively charged nucleic acids are released from cells and exposed to positively charged particles present in the environmental sample. The interaction between the negatively charged nucleic acid and positively charged particles can compromise a desired yield of nucleic acid from the isolation process. Thus, in certain embodiments, adsorption of nucleic acid is inhibited by the addition of a sodium phosphate buffer in the lysis solution. Specifically, a sodium phosphate buffer can be added to the lysis solution at a concentration of between 300 mM to 1.2 M; or between 500 mM to 1.0 M. For example, suitable concentrations of the sodium phosphate buffer are 300 mM, 400 mM, 500 mM, 600 mM, 700 mM, 800 mM, 900 mM, 1M, 1.1M and 1.2 M, and any value between these specific values. Additionally, sodium phosphate buffer is present at a neutral pH between 6.0 to 9.0, or between 7.0 to 8.0, inclusive. In specific embodiments, the sodium phosphate buffer present in the lysis solution is 600 mM $NaH_2PO_4$ with $Na_2HPO_4$ at pH 7.2, 1.0 M $NaH_2PO_4$ with $Na_2HPO_4$ at pH 7.2 or 1M $NaH_2PO_4$ with $Na_2HPO_4$ at pH 8.0.

In certain embodiments the lysis solution consists of: 4 M guanidine isothiocyanate; 100 mM Tris pH 7.0, 20 mM EDTA, 0.6% sarkosyl, and 10 µl/ml 2-mercaptoethanol; or, alternatively, 1 M sodium phosphate buffer (pH 7.2), 4 M guanidine isothiocyanate, 10 µl/ml 2-mercaptoethanol. In yet another embodiment the lysis solution contains: 1 M sodium phosphate buffer and 6 M guanidine HCl; or 1 M sodium phosphate buffer pH 8.0 and 6 M guanidine HCl.

An aspect of the current method includes obtaining a lysed material from an environmental sample containing cells, wherein the cells are lysed in the presence of liquid nitrogen. In certain embodiments, samples are loaded into sterile autoclaved mortars and dispersed with a pestle and overlaid with liquid nitrogen ($LN_2$), ground until thawed and collected from the mortar. In other embodiments the environmental sample is frozen with liquid nitrogen, ground until thawed, refrozen with liquid nitrogen and ground again until thawed. In another embodiment liquid nitrogen is applied more than twice and the subsequent frozen sample is ground until thawed repeatedly, prior to collection of the lysed material. In another aspect of the current methods lysis can occur by any method known by one skilled in the art, so long as the lysis method does not sheer (e.g., bead milling) or denature (e.g., heating the sample above 35° C., e.g., heating at 35° C., 40° C., 45° C., 50° C., 55° C., 60° C., 65° C. or higher) the nucleic acid during the lysis process. Non-limiting examples of lysis processes to be used in the current methods include physical, chemical, and enzymatic lysis or any combination thereof.

Extraction Process

Once the lysed material is obtained it is collected by washing into a collection vehicle (e.g., centrifuge tube) with extraction solution. Extraction solution as used in the current disclosure shall mean any solution containing, a chaotropic agent; an ionic buffer; and a chelating agent. Wherein, a chaotropic agent is any agent or substance that denatures molecules such as proteins or inhibits enzymatic activity. Non-limiting examples of chaotropic agents of the current methods include, urea, salt (e.g., NaCl), or alcohols such as phenol, or isoamyl alcohol. In certain embodiments the chaotropic agent is urea. Chaotropic agents can be added to a solution at any concentration necessary to disrupt or denature protein conformation. The concentration of chaotropic agents to be used in the current methods will vary depending on the amount and volume of sample being processed. Non-limiting examples of functional concentrations of chaotropic agents for use in the extraction process of the current methods include, 2 to 10 M urea, and 0.5 to 3M NaCl, inclusive. Ionic buffers for use in the extraction process are defined above. In specific embodiments the ionic buffer present in the extraction solution is MOPS. Chelating agents for incorporation into the extraction solution are listed above. Specifically, EDTA can be added to the extraction process for chelation of metal ions in the solution. Optionally, sodium phosphate buffer can be added to the extraction buffer at any concentration to improve the yield, quality and size of nucleic acid isolated from the sample. Non-limiting examples of sodium phosphate buffer concentrations useful in the current methods include, sodium phosphate buffer at a concentration between 0.1 M and 1.2 M, 0.1 M and 0.6 M, 0.3M and 1.0M, and 0.6 M to 1.0M.

In a specific embodiment the extraction solution for use in the current methods is 6.4 M urea, 1 M NaCl, 100 mM MOPS (pH 7.0), 40 mM EDTA; or 100 mM Tris; 1M NaCl; 100 mM sodium phosphate buffer, 20 mM EDTA, 1% SDS.

In certain embodiments the extraction process includes mixing the lysed materials with an extraction solution in the presence of a detergent. Detergents added during the extraction process act as dehydrating agents that promote precipitation of nucleic acids from solution. Detergents useful in the lysis process are similarly useful in the extraction process. Non-limiting examples of specific detergents for incorporation in the extraction process include sarkosyl, SDS, and CTAB.

In one aspect the extraction process includes, mixing the extraction solution with an equal volume of chloroform:isoamyl alcohol (49:1) and subjecting to centrifugation. In yet another embodiment the extraction solution is mixed with a solution containing phenol chloroform and spun via centrifugation to create an aqueous top lay containing nucleic acids and a lower liquid layer containing cellular byproducts and a sample pellet.

In certain embodiments the lysed materials are collected from the mortar by washing with extraction solution, subjected to centrifugation, and mixed with chloroform: isoamyl alcohol (49:1) and subjected to centrifugation leaving a sample pellet and supernatant containing nucleic acids. In yet another embodiment, the lysed materials are collected from the mortar by washing with extraction solution, mixed, subjected to centrifugation and treated with a detergent, again centrifuged, and mixed with chloroform: isoamyl alcohol (49:1) and subjected to centrifugation to obtain a pellet and supernatant containing nucleic acids. In certain aspects of the extraction process potassium acetate is added to the extraction mixture after the addition of the detergent, SDS to precipitate SDS and enable the detergent to be separated from the nucleic acid containing solution by a subsequent centrifugation.

In a certain embodiment the lysed materials are collected from the mortar by washing with extraction solution, containing either 6.4 M urea, 1 M NaCl, 100 mM MOPS (pH 7.0), 40 mM EDTA, or alternatively, 100 mM Tris; 1M NaCl; 100 mM $NaH_2PO_4$, 20 mM EDTA, 1% SDS; is mixed and subjected to centrifugation, and mixed with chloroform: isoamyl alcohol (49:1) and subjected to centrifugation leaving a sample pellet and supernatant containing nucleic acids. In yet another embodiment the lysed materials are collected from the mortar by washing with extraction solution, containing either 6.4 M urea, 1 M NaCl, 100 mM MOPS (pH 7.0), 40 mM EDTA, or 100 mM Tris; 1M NaCl; 100 mM $NaH_2PO_4$, 20 mM EDTA, 1% SDS; is subjected to centrifugation, a detergent mixture containing sarkosyl and CTAB is added to the mixture and the resulting solution is then mixed and treated with potassium acetate before being subjected to centrifugation and mixed with chloroform:isoamyl alcohol (49:1); and centrifuged leaving a sample pellet and supernatant containing nucleic acids.

Wash Process

An aspect of the current disclosure includes collecting the supernatant after completion of the extraction process and subsequent centrifugation, and washing the sample pellet with a wash solution. Washing as described herein facilitates desorption of negatively charged nucleic acids from the positively charged surface of particles contained within the environmental sample pellet. Wherein the wash solution used in the methods of the current disclosure contains at least 0.3 M sodium phosphate buffer. Non-limiting examples of wash solution useful for the current methods include sodium phosphate at a concentration in the range of 300 mM to 1.2 M; or 500 mM to 1.0 M. For example, suitable concentrations of the sodium phosphate buffer for use in the washing step are 300 mM, 400 mM, 500 mM, 600 mM, 700 mM, 800 mM, 900 mM, 1M, 1.1M and 1.2 M, and any value between these specific values. Additionally, the sodium phosphate buffer has a neutral pH between 6.0 to 9.0, or between 7.0 to 8.0, inclusive. In specific embodiments, the wash buffer consists of 1 ml/g [500 mM $NaH_2PO_4$ with $Na_2HPO_4$ at pH 7.2 or 1.0 M $NaH_2PO_4$ with $Na_2HPO_4$ at pH 7.2]. In certain embodiments, in addition to sodium phosphate, the wash buffer also contains one or more additional agents that contribute to stabilization of desorbed nucleic acid or further promote desorption. Examples of such additional agents include a chaotropic agent (e.g., urea, NaCl), a detergent (e.g., sarkosyl, SDS), serum albumin proteins (e.g., BSA), and a chelating agent (e.g., EDTA, EGTA).

In certain embodiments the sample pellet is washed in a sodium phosphate buffer mixed vigorously (e.g., vortex or shaking) and centrifuged to obtain a sample pellet and a supernatant containing nucleic desorbed nucleic acid. In another embodiment the wash step is repeated more than once. For example, the wash step is repeated twice, three times, four times, or greater.

In certain aspects the supernatant resulting from the wash step or steps is collected (e.g., centrifuge tube). In yet another aspect the supernatant collected from the wash step and/or additional wash steps are combined with the supernatant collected after the extraction process or previous washes. In one embodiment the supernatant collected after washing with sodium phosphate buffer is subjected to an extraction process (i.e., a repeat extraction process). In yet another embodiment the supernatant collected after the wash is subjected to nucleic acid precipitation directly.

In certain embodiments the method for isolating nucleic acid from an environmental sample includes lysing the cells in the presence of sodium phosphate buffer to reduce adsorption of nucleic acid to positively charged particles in the sample, subjecting the lysed materials obtained from the lysis process to an extraction process, washing the pellet obtained after centrifugation in phosphate buffer to desorb nucleic acids bound to cationic particles in the environmental sample; prior to isolating the nucleic acids via precipitation and subsequent purification steps. In other embodiments, the method for isolating nucleic acid from an environmental sample includes lysing the cells in a lysis solution without sodium phosphate buffer, subjecting the lysed materials to an extraction process, washing the pellet obtained after centrifugation in phosphate buffer to desorb nucleic acids bound to cationic particles in the environmental sample; prior to isolating the nucleic acids via precipitation and subsequent purification steps. In yet another embodiment the method for isolating nucleic acid from an environmental sample includes lysing cells in the presence of sodium phosphate to prohibit adsorption, subjecting the lysed materials obtained from the lysis process to an extraction process and subjecting the resulting supernatant to the subsequent precipitation and purification steps.

In certain aspects, sodium phosphate buffer is present in the extraction solution as well as the lysis solution and/or wash solution. For example, sodium phosphate buffer is present in the extraction step and wash solution but not the lysis solution. In yet another example sodium phosphate buffer is present in the extraction step and lysis solution but no wash step is conducted. In another example, sodium phosphate buffer is present in both the lysis solution and the extraction solution, and at least one wash step is conducted on the sample pellet.

Precipitation and Purification of Nucleic Acid

Nucleic acids extracted from the environmental sample using the current methods will be present in solution (i.e., supernatant(s)) resulting from the extraction process and/or wash step(s). In order to isolate the nucleic acid from the collected supernatants the nucleic acid must be precipitated in the presence of alcohol (e.g., isopropyl alcohol (isopropanol) and/or ethyl alcohol (ethanol)). A Non-limiting example of a nucleic acid precipitation process for use in the current methods includes the addition of isopropanol, mixing, and subsequent centrifugation creating a nucleic acid pellet and a supernatant. The supernatant is then discarded and the remaining nucleic acid pellet is purified.

Nucleic acid purification methods are well known to those of ordinary skill in the art. The methods of the present disclosure are amenable to use with any known purification method, including, but not limited to, ethanol washing, chromatography, gel filtration, QIAGEN AllPrep DNA/RNA kit, Sephadex™ G75 kits, Wizard™ DNA Clean-Up System (Promega, Madison, Wis.), PowerSoil™ DNA CleanUp reagents (MoBio), QIAGEN Total Nucleic Acid purification system, SV Total RNA isolation system (Promega, Madison, Wis.), NucleoBond system (Clontech, Palo Alto, Calif.) and RNA Tack Resin (BIOTECX laboratories, Houston, Tex.).

In a specific embodiment the precipitated nucleic acid pellet is washed one or more times with between 70% and 100% ethanol.

After the nucleic acid precipitation, the nucleic acid pellet is resuspended into solution. In certain embodiments the nucleic acid pellet is suspended in diethylpyrocarbonate (DEPC) treated $H_2O$. In yet another embodiment the nucleic acid pellet is suspended in Tris-EDTA buffer (TE buffer) at a pH from 7.0 to 8.1.

The current methods do not heat the sample at to a temperature that would denature the nucleic acid (i.e., above 35° C.) or employ lysis techniques that sheer nucleic acid (i.e., bead milling), and thus nucleic acid isolated by the current methods are typically of high molecular weight (≥20 kb). The isolated nucleic acid isolated via the current methods will be of sufficient quality and quantity enabling the nucleic acids to be analyzed as desired by the end user.

In certain aspects, the nucleic acid comprises RNA, and the RNA can be reverse transcribed into cDNA after precipitation of the isolation procedure. In yet another aspect, the nucleic acid is contacted with a restriction enzyme and digested after precipitation of the isolation procedure.

In one aspect, the isolated nucleic is analyzed by mass spectrometry; agarose, capillary or polyacrylamide electrophoresis; hybridization; an array; a microarray; an enzymatic reaction; a fluorescent assay; a radioactive assay; a chromatographic assay; or, a combination thereof. In one aspect, the nucleic acid is contacted with one or more oligonucleotides after precipitation of the isolation procedure. In certain aspects, one or more of the oligonucleotides hybridizes to the nucleic acid. In one aspect, a nucleic acid is immobilized to a solid surface or is hybridized to a nucleic acid immobilized on a solid surface.

In an aspect of the current disclosure, the methods or kits or the invention can further comprise amplifying the nucleic acid or a portion thereof after precipitation of the isolation procedure. In one aspect, the nucleic acid is amplified using a polymerase chain reaction (PCR) procedure, rolling circle replication, ligase-chain reaction or derivative methods thereof. In a specific embodiment, the isolated nucleic acids are amplified using pyrosequence tagged primers targeting regions of the 16s rRNA gene to evaluate the diversity of species present in an environmental sample.

A non-limiting example of species diversity evaluation for use in conjunction with the current methods is quantification of the bacterial 16S rRNA genes using the V1/V3 region for pyrosequencing with the Titanium™ 454 chemistry. See, e.g., Krober et al., 2009; Voelkerding et al., 2009; Nossa et al., 2010; Ishak et al., 2011. Whereby, the 16s rRNA gene is amplified utilizing primers containing pyrosequencing tags that, when incorporated in to an amplified target sequence, are used to identify individual species of interest and thus can be used to quantify the number of species present in the isolated nucleic acid obtained from an environmental sample of interest. The amplification products (amplicons) are then evaluated using gel electrophoresis, purified using magnetic particle separation and evaluated for concentration and purity. The amplicons are then sequenced using known methods (e.g., 454 Life Sciences Titanium™ gene sequencer system) and the samples are then compared and analyzed to determine species distinctions present. Analysis optionally includes, the removal of; sequencing errors (e.g., AmpliconNoise algorithm), chimeric sequences using UCHIME, and sequence alignment and trimming to recognize the sequence of interest. See Edgar et al., *Bioinform* (2011) 27: 2194-2200.

In other aspects the nucleic acid isolated via the current methods are of sufficient quality and quantity to enable use in systems biology studies including, but not limited to microbial community genomic and transcriptomic studies.

The current disclosure provides kits for isolating nucleic acids from an environmental sample containing. The methods and kits of the invention are applicable to a variety of nucleic acid preparations (e.g., TruRNA™ Atom Sciences, Oak Ridge, RNA PowerSoil™, and Powerlyzer™ MoBio Laboratories, Salona Beach, Ca). The kits and methods of the current disclosure are adaptable to a wide range of sample volume, mass and type and nucleic acid yield.

EXAMPLES

The following examples further illustrate the disclosure, but should not be construed to limit the scope of the disclosure in any way.

Example 1

Methods and Materials

Collection of Soil and Sediment Samples.

Three stream sediment core samples were taken from kilometer 5 and 22.3 of East Fork Poplar Creek (EFPC and Hinds Creek, Oak Ridge Tenn., at a depth of 45 cm. The cores were frozen in the field in liquid nitrogen and stored at −80° C. until nucleic acids were isolated from the samples. These cores were heterogeneous in texture and consisted largely of gravel, sand, coal fragments, and iron cemented clay. To prevent loss of precious test sediment, alternative samples containing iron cemented clay were used for method development. A clay sample was taken at 20 cm below the surface of deciduous forest A-horizon in Knoxyille, Tenn. and maintained at 21° C. for >3 days. The top two inches of A-horizon soil was used to evaluate the reagents and ensure that nucleic acids within were protected throughout the extraction process. The iron cemented clay had a uniform appearance and nucleic extractions were performed on 250 mg samples that were taken from larger pieces of core samples by removing portions of the exterior via a sterile spatula. A-horizon samples were placed in a plastic bag, root and other material present in larger pieces were removed, and the residual soil was manually mixed to prepare a uniform loamy material.

Carbon, Nitrogen and Iron Content Determination.

All samples including the deciduous forest surface and sub-surface soil samples used for process development were determined for total organic carbon and nitrogen content by combusting about 0.2 g soil at 950° C. using a LECO TruSpec CN Determinator 630 (LECO Co, MI) (Table 3). Acid extractable iron content was determined by suspending 0.5 g (dry weight) soil or sediment in 5 ml of 0.5 M HCl shaking vigorously for 4 h, followed by centrifugation at 600×g for 15 minutes to obtain the clear supernatant (or acid extract). In addition, the total iron content was determined by digesting 0.5 g soil or sediment (dry weight) in 1 ml concentrated $HNO_3$ (67-70%) and 0.5 ml concentrated HCl (37.9%) at 95° C. for 4 hours, followed by dilution with deionized water to a final volume of 5 ml as per Luo and Gu, 2011. Total metal content in the acid extracts and digests was determined, after appropriate dilutions (10-100×), using an inductively coupled plasma mass spectrometer (ICP-MS, Elan-DRC, Perkin-Elmer, CT) (Table 3). Working standards were prepared in the range from 0.1 to 10 mg/L in dilute $HNO_3$ (0.01 M).

Nucleic Acid Extraction Process and Modification.

Frozen stream sediment samples or live room temperature clay samples and A-horizon samples used for method development were loaded into sterile autoclaved mortars and overlaid with standard lysis solution (4 M guanidine isothiocyanate; 100 mM Tris pH 7.0, 20 mM EDTA, 0.6% sarkosyl, 10 µl/ml 2-mercaptoethanol) or clay lysis solution (1 M phosphate buffer (pH 7.2), 4 M guanidine isothiocyanate, 10 µl/ml 2-mercaptoethanol) at a volume of 0.33 ml/g sample at 21° C. Lysis solution modifications were tested, including the addition of sodium phosphate buffer (see below) at final concentrations ranging from 100 mM to 1.2 M, the removal of the sarkosyl, and inclusion of serum albumin (BSA). Samples were dispersed for <5 seconds using a pestle and overlaid with liquid nitrogen ($LN_2$), ground until thawed twice, and washed from the mortar into centrifuge tubes with concentrated urea extraction buffer (4.67 ml/g sample; 6.4 M urea, 1 M NaCl, 100 mM MOPS (pH 7.0), 40 mM EDTA) or, alternatively, concentrated salt based extraction buffer (100 mM Tris; 1M NaCl; 100 mM $NaH_2PO_4$, 20 mM EDTA, 1% SDS).

Extraction solutions were centrifuged (4500×g, 10 min, 21° C.) in a bench top centrifuge (large scale preparations), or in a micro-centrifuge (10,000×g, 1 min, 21° C.; small scale preparations) depending on the sample quantity. A detergent mixture (5% sarkosyl and 5% cetyltrimethylammonium bromide) was added (1.3 ml/g), followed by 5 M potassium acetate (0.67 ml/g, pH 5.2). The resulting solutions were extracted by vigorous mixing with an equal volume of chloroform:isoamyl alcohol (49:1) and centrifugation (7,100×g, 20 min, 21° C.).

Total nucleic acids were precipitated with isopropyl alcohol (0.67 volumes), centrifuged (16,000×g, 20 min, 21° C.), and dissolved in diethylpyrocarbonate (DEPC) treated ddH2O.

For samples containing a large quantity of clay particles, the pellets were resuspended in 1 mug phosphate buffer [500 mM $Na_2HPO_4$, 500 mM $NaH_2PO_4$ (pH 7.2)] by vigorous agitation or brief vortex mixing and centrifuged at 10,000×g for 1 min. The solution was transferred to a new centrifuge tube, diluted with 2.33 ml/g extraction buffer and handled as described for the initial extraction. Nucleic Acids were precipitated using 0.67 volumes of isopropyl alcohol (21° C., 20 min) and centrifuged (16,000×g, 20 min at 21° C.). Precipitates were dissolved in DEPC treated ddH2O (100 µl/g). Humic acid removal was performed using a 1 cm column of Sephadex G-75 molecular exclusion resin (GE Healthcare) supplemented with 0.01 volumes of DEAE Sepharose (Sigma) diluted 1:10 in 500 mM potassium acetate. The column flow-through was collected and where visible discoloration was present, samples were further purified using solutions 1-4 of a MoBio® DNA cleanup system.

Three commercial reagent systems for extraction of TNA (TruRNAT™ Atom Sciences, Oak Ridge) and RNA (RNA PowerSoil™, and Powerlyzer™; MoBio® Laboratories, Salona Beach, Ca) were compared for nucleic acid recovery from soil sediment samples and clay samples. Additionally, selected published methods were compared including the methods described herein as OU (See Zhao, J., et al., *Appl. Environ. Microbiol.* (1996) 62: 316-322), MSU (See Hwang, C. et al., The ISME Journal (2009) 3, 47-64), H01 (See Hurt et al., *Appl. Environ. Microbiol.* (2001) 67: 4495-4503), CTABIPA (See DeAngelis, K. M., et al., *Appl. Environ. Microbiol.* (2011) 77(18):6313.) and PA-D (See Andeer et al., *Appl. Environ. Microbiol.* (2012) 78: 163-169). All purchased reagent systems were used according to the manufacturer's protocols.

Extraction Process Dependence of Microbial Community Composition.

Three methods that supported DNA recovery from deciduous forest iron-cemented clay and A-horizon soil were compared on the basis of recovered microbial diversity in replicate DNA extractions. All extractions of DNA from clay and A-horizon samples used for comparison of accessed microbial communities were performed on the same day. Community structure was evaluated by quantification of the bacterial 16S rRNA genes using the V1V/3 region for pyrosequencing with the Titanium™ 454 chemistry. (See Krober et al., *J Biotechnol.* (2009) 142: 38-49; Voelkerding et al., *Clin. Chem.* (2009) 55: 641-658; Nossa et al., *World J. Gastroenterol.* (2010) 16: 4135-4144; Ishak et al., *Microb. Ecol.* (2011) 61: 821-831. The 16S rRNA gene specific region of the PCR primers FLXA_27F 5'-cgt atc gcc tcc ctc gcg cca tca gAG AGT TTG ATC CTG GCT CAG-3' [SEQ. ID NO.: 1] and FLX_B534R 5'-cta tgc gcc ttg cca gcc cgc tca gcg caa cTY ACC GCG GCT GCT GG-3' [SEQ. ID NO.: 2] is shown in uppercase with the sequence tag identifying the sample shown in bold for one of the reverse primers. Primary amplification used 10 ng of purified DNA ($2.15 \times 10^6$ *Escherichia coli* genome equivalents) with Platinum® Taq DNA polymerase High Fidelity (Invitrogen®) for 27 dissociation cycles at 95° C.×30 seconds, annealing at 55° C.×30 seconds, and extension at 68° C.×30 seconds. The amplification products were evaluated by electrophoresis, purified using magnetic particle separation (AgenCourt® AMPure®XP, Beckman Coulter) and re-evaluated for concentration and purity using an Agilent 2100 BioAnalyzer™ (Agilent Technologies, Inc. Santa Clara, Calif.) and Pico-Green (Promega, Sunnyvale, Calif.) in a Synergy MX Multi-Mode Reader (BioTek). The V1-V3 amplicons were then sequenced using a 454 Life Sciences Titanium™ gene sequencer system according to manufacturer instructions (454 Life Sciences-Roche, Branford, Conn.). All compared amplification products were multiplexed onto a single 454 pyroseqeuncing run. Two libraries amplified from A-Horizon soil samples failed to produce a comparable number of sequences in the multiplexed pyrosequencing file and were discarded.

Pyrosequencing errors were removed using the Amplicon-Noise algorithm as described in Quince et al., 2011. See Quince et al., *BMC Bioinform.* (2011) 12: 38. The high quality sequences were binned based on barcodes using QIIME (See Caporaso et al., *Nat. Meth.* (2010) 7: 335-336) and the sequences were aligned against the bacterial SILVA database and trimmed to the same length using Mothur v 1.22.1. See Schloss et al., *Appl Environ. Microbiol.* (2009) 75: 7537-7541. Chimeric sequences were flagged and removed using UCHIME in Mothur. See Edgar et al., *Bioinfor.* (2011) 27: 2194-2200.

Clustering, Taxonomic Classification, and Statistical Analysis.

The final processed sequences were assigned to OTUs at 3% distance using average linkage clustering in Mothur. A representative sequence from each OTU was selected using QIIME (See Caporaso et al., 2010) and assigned to consecutive taxa using the Ribosomal Database Project (RDP) Classifier with a confidence cutoff of 0.5 (See Wang et al., *Appl. Environ. Microbiol.* (2007) 73: 5261-5267; Cole et al., 2009). Overlapping OTUs were calculated across replicates of the three compared extraction methods and across A-horizon and clay samples using the Venn Diagram package in R statistical software. See Chen and Boutros, *BMC Bioinform.* (2011) 12: 35. Rarefaction analysis comparing extraction methods for clay and A-horizon samples was performed by plotting the results of random sequence re-sampling. Outliers (OTUs identified only once across all samples) were removed to support a comparison with prior work that examined the utility of pyrosequencing-based taxon identification microbial community determination. See Zhou et al., *ISME* (2011) 5: 1303-1313. Rarefaction curves and overlapping OTUs were re-calculated after removing outliers.

Example 2

Extraction Process and Modification

Known nucleic acid extraction methods were carried out on stream sediment core samples obtained from East Fork Poplar Creek (EFPC). The results of the extractions using known methods failed to produce DNA of sufficient quantity or quality necessary for use in molecular analysis. The EFPC stream sediment samples largely consisted of a mixture of gravel and iron cemented clay as indicated by a rust color after exposure to air. For development of the current method, surface A-horizon soil was obtained from deciduous forest and its subsurface iron cemented clay (clay sample) was used. The clay sample had a uniform texture and a consistent moisture content of 24% at depths>15 cm below the surface. Initial nucleic acid extraction from the clay sample using known methods devoid of sodium phosphate buffer was not productive, and the similarity in color (red) to the refractory EFPC stream sediments suggested a common source of difficulty. The stream sediments contained coal fragments that caused a high percent of total carbon; however, the control site (Hinds Creek) consistently yielded a large quantity of co-extracted humic acid as well (Table 3). The A-horizon sample had the largest quantity of co-extracted organic matter; however, coal fragments were not present resulting in a lower total carbon measurement (Table 3). Although the clay sample had the lowest quantity of acid extractable iron (0.08 mg/g) it contained the highest total iron (38.66 mg/g) following acid digestion, demonstrating that essentially all available iron was in the form of crystalline iron oxides cemented with the clay. The surface (A-horizon) soil above the iron cemented clay was used as a positive control to insure that extraction systems were functioning to expectation. Like the clay sample, the A-horizon sample also contained a large amount of iron (Table 3).

Tests performed using a standard lysis solution (4 M guanidine isothiocyanate; 100 mM Tris pH 7.0, 20 mM EDTA, 0.6% sarkosyl, 10 µl/ml 2-mercaptoethanol) yielded DNA from the deciduous forest A-horizon, but no detectable DNA from the clay sample (FIG. 1). Triplicate extractions using the methods of the current disclosure in combination with either the RNA PowerSoil™ (FIG. 1, lanes 1-4) or TruRNA™ (FIG. 1, lanes 5-8) kits supported the simultaneous recovery of DNA and RNA from the A-horizon soil (FIG. 1, lanes 3, 7) and RNA recovered exhibited good 23S/16S rRNA stoichiometry indicating an absence of nucleic acid degradation during the extraction process. RNA PowerSoil™ reagents (MoBio) alone yielded some nucleic acids from one of the stream sediments (FIG. 1, lane 1) but no detectable DNA from the second stream sediment (FIG. 1, lane 2) or the clay sample (FIG. 1, lane 4).

The effect of pH on total nucleic acid (TNA) extraction from iron oxide cemented clay was tested over a range of 5.2 to 8.0. The entire range of standard Tris buffered lysis reagent, including unadjusted 200 mM Tris-HCl (pH 3.9) and unadjusted 200 mM Trizma base (pH 10.0), did not block nucleic acid adsorption to iron cemented clay. The effect of omitting sarkosyl from lysis reagent modified with 300 mM sodium phosphate buffer (PB) pH 7.2 resulted in a lower yield of DNA from clay samples, while inclusion of 10% BSA resulted in a larger quantity of extracted DNA as shown in electrophoretic images (FIG. 1C).

Ionic interaction tests using modified lysis solutions containing; 1) 2 M sodium chloride, 2) 1 M ammonium sulfate, and 3) 1 M ammonium phosphate, yielded no measureable DNA or RNA from the clay samples and concentrated sodium chloride caused problematic clay sample expansion, limiting recovery of the solution. Post-lysis washes with concentrated ammonium sulfate (pH 7.0) and ammonium phosphate (pH 7.0) failed to yield nucleic acids from the stream sediments or clay samples, and also blocked extraction of discoloring soil organic matter.

After the initial non-productive extraction (FIG. 2A; lanes 1), high molecular weight DNA could be desorbed from iron oxide cemented clay by suspension with a 1:1 clay weight/ 1M phosphate buffer volume (500 mM $Na_2HPO_2$, 500 mM $NaH_2PO_4$ pH 7.2), followed by an additional centrifugation (10,000×g, 1 min, 20° C.; FIG. 2A; lanes 2). A second pellet wash with phosphate buffer solution was productive (FIG. 2A; lanes 3) while a third wash was found to offer a negligible yield. The DNA from the stream sediment cores recovered using this the presently discovered phosphate buffer desorption method showed a high molecular weight electrophoretic migration profile where the small amount of DNA visible in ethidium bromide Tris-Acetate electrophoresis (TAE) gels was highly fragmented for both liquid nitrogen grinding and bead mill preparative methods used without phosphate buffer desorption. Surprisingly, when the phosphate buffer was applied high molecular weight DNA was extracted. For example, 1.1 µg±0.1 µg high molecular weight DNA/gram sediment from the mile 5.0 EFPC stream sediment cores, 0.6 µg±0.1 µg high molecular weight DNA/gram sediment from the mile 22.3 EFPC stream sediment cores, and 0.5 µg±0.0 µg high molecular weight DNA/gram sediment from the background control site stream sediment cores, whereby prior to the currently disclosed phosphate buffer desorption method, the yield from all preparations using as much as 5 g of stream sediment was undetectable using spectrophotometer $A_{260}$ measurement.

Using a concentrated salt based extraction buffer required additional steps due to phosphate precipitation with 0.6 volumes of isopropanol. A lysis reagent consisting of 1 M phosphate buffer pH 8.0 and 6 M guanidine HCl yielded DNA during the initial extraction where 1.4 ml of a concentrated salt buffer (100 mM Tris-HCL (pH 8.0), 100 mM sodium EDTA (pH 8.0), 100 mM sodium phosphate (pH 8.0), 1.5 M NaCl, 1% hexa-decylmethylammonium bromide) was used to wash the sample from the mortar (FIG. 2B, lanes 1). Suspension of the clay pellet in 1 M phosphate buffer (pH 7.2) followed by centrifugation that yielded additional larger DNA fragments (FIG. 2B, lanes 2). Taken together these findings revealed stronger adsorption of longer DNA fragments which required increased phosphate concentrations for desorption. A second wash sodium phosphate buffer did not yield additional measurable nucleic acid recovery, showing that efficient extraction can be accomplished with a single phosphate buffer wash when 1 M sodium phosphate is used in the lysis reagent.

Extraction from iron cemented clay yielded no measurable nucleic acids with either TruRNA™ reagents (Atom Sciences) or PowerLyzer™ reagents (MoBio) when extraction tests were performed on the same day the samples were recovered from their natural environment. Triplicate extractions using a gradient of phosphate buffer concentrations in the lysis reagent were performed to determine the optimal total nucleic acid recovery concentration. No phosphate buffer in the lysis solution resulted in no nucleic acid recovery (FIG. 3A, lane 1), while some DNA was obtained with 100 mM phosphate buffer (FIG. 3A, lane 2), and as the phosphate buffer concentration increased, an increase in both the extracted DNA concentration and DNA fragment length was observed (FIG. 3A, lanes 3-6). The amount of DNA recovered from the phosphate buffer wash was similar to the re-wash of the pellet obtained with phosphate in the lysis solution, demonstrating that lysis was effective with or without phosphate in the lysis reagent. DNA from the initial extraction procedure was kept separate from the 1 M sodium phosphate buffer wash result and both fractions were purified using a Power-Clean™ DNA Cleanup kit (MoBio). Despite DNA loss during purification, the total yield was larger from the grinding process (7.96±3.03 μg/g clay) Agarose gel purification with the Wizard™ DNA Clean-Up System (Promega) supported improved recovery of high molecular weight fraction yielding 15.22±2.33 μg/g clay.

Example 3

Known Nucleic Acid Extraction Procedures were Compared to the Current Method for Recovering High Molecular Weight DNA from Clay Environments Known procedures that used extraction reagent heating with iron cemented clay resulted in excessive DNA fragmentation (FIGS. 4C and 4D). The yield of DNA from known methods varied based on the method for final purification prior to quantification. For example, the OU and MSU methods consist of the same nucleic acid extraction followed by gel purification (OU) or use of PowerSoil™ DNA CleanUp reagents (MoBio) (MSU). Excessive DNA fragmentation in samples heated in the presence of iron cemented clay (65° C.×2 h) resulted in poor yield from agarose gel purification (OU and MSU FIG. 4, FIGS. 4C and 4D) as shown by high molecular weight being retained in the gel comb well. Conversely, the binding and washing purification methods of the current disclosure showed extensive high molecular weight DNA recovery. Despite shearing, lysis by liquid nitrogen grinding yields larger DNA fragments than bead milling, and while the PA-D method uses a modified bead milling procedure, resulting in a high yield of DNA from the iron cemented clay (FIG. 4), the DNA was fragmented. Overall, while the presently described method and the PA-D methods resulted in the highest yields of DNA from clay samples and A-horizon soils, only the current method was the was capable of maintaining the high molecular weight nucleic acids critical for sequencing (FIG. 4).

Example 4

Comparison of Accessed Microbial Community Diversity

Triplicate DNA extractions for each of the ORNL 2001 method (See Hurt et al., 2001), the method of the current disclosure, and the PowerLyzer™ reagents (MoBio) method were amplified using pyrosequence tagged primers targeting the V1-V3 region of the 16S rRNA gene. The amplicons were then processed via removing pyrosequencing errors using the AmpliconNoise algorithm. Then high quality sequences were binned based on barcodes using QIIME and the sequences were aligned against the bacterial SILVA database and trimmed to the same length using mothur v 1.22.1. Chimeric sequences were then flagged and removed using UCHIME in mother resulting in a total of 61,674 high-quality bacterial DNA sequences (mean=3855 reads; n=16) (Table 2). An average of 828±28 operational taxonomic units (OTU) were obtained for the A-horizon. A conventional confidence threshold of 50% was used for OTU assignment using the RDP classifier algorithm that assigns sequences to recognized taxa that are a closely matched in the Ribosomal Database Project due to the short length (≥250 nucleotides) of the processed sequences. The amount of unassigned clay sample OTU's identified by the current method were 46.2±3.2% using a confidence threshold of 95%. However, at the default 80% confidence threshold, the number of unclassified sequences dropped to 35.0±2.8%, and at a 50% confidence threshold the unclassified OTU's dropped to 19.2±3.2%.

To compare the total recovered species diversity among the methods, rarefaction curves were prepared from lists generated using Mothur online sequence analysis software (FIG. 5). The averaged rarefaction curves showed that the recovered diversity was approximately 1.8-fold higher with the presently described extraction method for A-horizon soils and 4-fold higher when applied to clay samples. Variation among experimental replicate extractions showed that the diversity accessed was reproducible for a given method. The average OTU's at 2,500 and 5,000 reads (Table 1) indicate a flattened plateau in the rarefaction plots that may require combining libraries from additional PCR amplifications.

The Firmicutes exhibit a higher proportion in libraries derived using the current extraction method compared to previously known extraction methods while the OTU's identified as Firmicutes in the iron cemented clay samples was greater than 6-fold larger than those recovered using the PowerLyzer™ reagents and ~8-fold larger than the ORNL 2001 method. The larger representation of Firmicutes was also apparent in the increased diversity from the A-horizon sample. Additionally, the methods of the current disclosure also yielded the largest number of unclassified OTU's (FIG. 6). Taken together, the improved capacity to recover DNA from the Firmicutes and large number of unclassified OTUs indicates the current extraction method is capable of accessing bacterial species that are more difficult to lyse, and thus provide a marked advantage over previously known methods.

Venn diagrams using de-noised data with data outliers removed show a higher proportion of overlapping OTUs were recovered using the current DNA extraction method (FIG. 7), revealing improved coverage of the microbial community present in a sample. For example, OTUs recovered from clay samples using the current methodology overlapped with 63.1% of the OTUs accessed with the PowerLyzer™ procedure, whereas only 32% of the OTUs present from the PowerLyzer™ procedure were also present using the current extraction method. The ORNL 2001 method yielded a smaller number of identified OTUs than the libraries resulting from the PowerLyzer™ procedure (FIG. 7), and showed a larger percentage overlap (36.1%) with the libraries produced using the current extraction method. This finding is not a result of probability because a larger total number of OTUs from the ORNL 2001 libraries (449 OTUs) overlap with the libraries produced using the current extraction method than the libraries generated from DNA prepared using the PowerLyzer™ procedure (399 OTUs).

TABLE 1

|  | Clay | | A-horizon | |
| --- | --- | --- | --- | --- |
| Method | OTU's/2500[A] | OTU's/5000[A] | OTU's/2500[A] | OTU's/5000[A] |
| Hurt, 2001 | 369.5 ± 59.5 | 567.5 ± 125.6 | 732.7 ± 9.7 | 1104.6 ± 28.7 |
| Current Method | 966.0 ± 115.5 | 1647.8[B] ± 199.0 | 944.6 ± 46.5 | 1531.2 ± 103.8 |
| PowerLyzer ™ | 431.7 ± 54.4 | 618.0 ± 132.2 | 794.1 ± 15.6 | 1231.4[C] |

TABLE 2

| Sample | Nitrogen % | Carbon % | Acid Ext. Fe mg/g$^a$ | Fe mg/g$^b$ | Al mg/g$^b$ |
|---|---|---|---|---|---|
| Clay | 0.078 | 0.370 | 0.08 | 38.66 | 12.30 |
| A-horizon | 0.045 | 0.502 | 0.58 | 21.25 | 5.90 |
| 22.3 EFPC | 0.105 | 1.235 | 2.12 | 7.51 | 4.85 |
| 5.0 EFPC | 0.106 | 0.737 | 2.16 | 8.16 | 4.13 |
| Background | 0.379 | 5.750 | 1.08 | 4.66 | 4.34 |

TABLE 3

| Method | Clay µgDNA/g | A-Horizon µgDNA/g | Final Purification Procedure |
|---|---|---|---|
| OU | 9.63 ± 1.03 | 45.21 ± 6.50 | Gel Purification by Phenol Extract |
| Current Method | 15.22 ± 2.33 | 189.07 ± 33.69 | Gel Purification/ Promega Wizard Modified Elution |
| MSU | 2.31 ± 0.23 | 20.90 ± 3.77 | MoBio PowerSoil ™ DNA Cleanup |
| H01 | 6.06 ± 3.06 | 10.10 ± 5.46 | Gel Purification/ Promega Wizard |
| CTABIPA | 0 | 28.86 ± 10.28 | QIAGEN All Prep DNA/RNA |
| PA-D | 19.84 ± 1.23 | 182.4 ± 15.26 | Digestion with RNase A |
| PowerLyzer ™ | 2.04 ± 0.54 | 13.2 ± 3.48 | PowerLyzer ™ |

What is claimed is:

1. A method for isolating nucleic acids from an environmental sample, comprising:
   (i) obtaining an environmental sample comprising cells;
   (ii) subjecting the sample to a lysis process comprising mixing the sample with a lysis solution in the presence of liquid nitrogen, thereby obtaining a lysed material;
   (iii) subjecting the lysed material to an extraction process by mixing the lysed material with an extraction solution, and subjecting the resulting mixture to centrifugation;
   (iv) collecting the supernatant after the centrifugation;
   (v) washing the pellet obtained after the centrifugation of step (iii) with a wash solution comprising sodium phosphate at a concentration of at least 300 mM, and collecting the supernatant from the wash; and
   (vi) combining the collected supernatants from step (iv) and step (v), and isolating nucleic acids from the collected supernatants.

2. The method of claim 1, wherein the environmental sample is selected from the group consisting of soil, clay, sediment, water or liquid, and a combination thereof.

3. The method of claim 1, wherein said lysis solution comprises sodium phosphate at a concentration of at least 300 mM.

4. The method of claim 1, wherein said cells are bacterial cells.

5. The method of claim 1, wherein said cells are eukaryotic cells.

6. The method of claim 5, wherein said cells are selected from fungal cells or mammalian cells.

7. The method of claim 1, wherein said pellet is washed in step (v) more than once.

8. The method of claim 1, wherein said lysis solution further comprises a denaturing agent, an ionic buffer, and a chelating agent.

9. The method of claim 8, wherein said denaturing agent is guanidine isothiocynanate or phenol.

10. The method of claim 8, wherein said lysis solution further comprises serum albumin protein and/or a detergent.

11. The method of claim 1, wherein said extraction solution comprises a chaotropic agent, an ionic buffer and a chelating agent.

12. The method of claim 11, wherein said chaotropic agent is urea or a salt.

13. The method of claim 11, wherein said ionic buffer is 3-(N-morpholino)propanesulfonic acid (MOPS), 2-[4-(2-hydroxyethyl)piperazine-1-yl]ethanesulfonic acid (HEPES), or trihydoroxymethyl aminomethane (Tris).

14. The method of claim 11, wherein said chelating agent is EDTA.

15. The method of claim 1, wherein the extraction solution comprises urea, MOPS, NaCl and EDTA.

16. The method of claim 1, wherein sodium phosphate is included in the lysis solution at a concentration between 0.5M and 1.2M.

17. The method of claim 1, wherein sodium phosphate is included in the wash solution at a concentration between 0.5M and 1.2M.

18. The method of claim 1, wherein said lysis solution comprising sodium phosphate has a pH of 7.0-8.0.

19. The method of claim 1, wherein the method is performed at temperatures not higher than 35° C.

20. The method of claim 1, wherein said lysis process comprises the use of a physical means.

21. The method of claim 20, wherein said physical means comprises grinding with a pestle and mortar.

22. The method of claim 1, wherein the nucleic acids isolated comprise nucleic acids of at least 20 kb in size.

23. The method of claim 1, wherein nucleic acids are isolated from the collected supernatants in step (vi) by precipitating the nucleic acids from the collecting supernatants using isopropyl alcohol (isopropanol) and/or ethyl alcohol (ethanol).

24. A kit for extracting nucleic acids from an environmental test sample comprising a sodium phosphate wash buffer, wherein said sodium phosphate wash butter comprises at least 0.3 M sodium phosphate and instructions describing a method for isolating nucleic acids from an environmental sample as set forth in claim 1.

* * * * *